(12) United States Patent
Webster et al.

(10) Patent No.: US 6,326,182 B1
(45) Date of Patent: Dec. 4, 2001

(54) ISOLATED HUMAN LIPASE PROTEINS, NUCLEIC ACID MOLECULES ENCODING HUMAN LIPASE PROTEINS, AND USES THEREOF

(75) Inventors: Marion Webster, San Francisco, CA (US); Ellen M. Beasley, Darnestown; Valentina Di Francesco, Rockville, both of MD (US)

(73) Assignee: PE Corporation (NY), Norwalk, CT (US)

(*) Notice: Subject to any disclaimer, the term of this patent is extended or adjusted under 35 U.S.C. 154(b) by 0 days.

(21) Appl. No.: 09/821,736

(22) Filed: Mar. 30, 2001

(51) Int. Cl.[7] .............................. C12N 9/20; C12N 1/20; C12N 15/00; C12Q 1/68; C07H 21/04

(52) U.S. Cl. .................. 435/198; 435/252.3; 435/320.1; 435/6; 536/23.2

(58) Field of Search ................................. 435/198, 252.3, 435/320.1, 6; 536/23.2

(56) References Cited

PUBLICATIONS

Parsonage et al. The Jouranl of Biological Chemistry, vol. 273, No. 37, pp 23812–23822. (Sep., 1998).*

Matsuoka et al. JP10150985–A. Sep., 1998. (English translation).*

* cited by examiner

Primary Examiner—Ponnathapu Achutamurthy
Assistant Examiner—Yong Pak
(74) Attorney, Agent, or Firm—Celera Genomics; Robert A. Millman; Justin D. Karjala

(57) ABSTRACT

The present invention provides acid sequences of peptides that are encoded by genes within the human genome, the lipase peptides of the present invention. The present invention specifically provides isolated peptide and nucleic acid molecules, methods of identifying orthologs and paralogs of the lipase peptides, and methods of identifying modulators of the lipase peptides.

10 Claims, 14 Drawing Sheets

```
   1 GATTTTAGTC CCAGACAGCC GAGCCAGATC CGGGGCGAAC GCAAAGAACA
  51 GAGGGAGAAG GGGAGCAGGG AGGCGAGAGG AGGGCAGTAC ATGTAAGCCA
 101 GGTCAACAGA GGCACATCAC GGACTAAAGA AGCGGGACAG GCGGGGGAAG
 151 AAGAAGAAAA AGAAAGGGTA ACCCTAAAAC GAGAAGCGGC GGGAGGCGAC
 201 AAGCTTAAGA CCGGTACAGG ACGAGAAAAC CCAAGCAATA ATACCCCCCA
 251 GCAAAAAGGA GTATAGTTCC AGCGAAAGAG CGAAACGGAT ATCTACACGC
 301 CGGCGAACAC GACCACGGGA CGCAGAGAGC AAGGCAAAAG AAAAAAAGG
 351 TGTAAAGAAG CAGGGGAGCG GACCTGGGAA GGGCGACAGA GAGGGGGAAG
 401 CAACCATAGA CGGCCTGGAC ATAAATGAGC CTGGCAACAG CAGCGCGCGT
 451 TCGCAGTAGA AGACCCTCTA TGGGTCGCGG GCAGGCAAGG GGTCGCTGTG
 501 CACATCCCTG CAGCGGTTGG CCACCCTGTG AAACTGAGAG TCCTCCATTG
 551 CATCTTCCAG CTGCTGTTGA CTTGGGGGAT GATATTTGAG AAGCTCAGAA
 601 TCTGTTCTAT GCCCCAATTT TTCTGTTTCA TGCAAGATCT GCCTCCGCTA
 651 AAGTATGACC CCGATGTTGT GGTCACGGAT TTCTGCTTTG GGACAATCCC
 701 TGTGAAGCTG TACCAACCCA AGGCATCCAC CTGCACCCTG AAGCCTGGCA
 751 TCGTGTACTA CCACGGTGGC GGGGGCGTCA TGGGGAGTTT GAAAACCCAC
 801 CATGGCATAT GCTCTCGTTT GTGCAAGGAG AGTGACTCCG TGGTTCTGGC
 851 AGTTGGTTAC CGCAAGTTAC CTAAGCATAA GTTTCCAGTG CCAGTAAGAG
 901 ACTGCTTGGT GGCCACCATC CACTTCCTGA AGTCCCTGGA TGCATATGGA
 951 GTGGATCCAG CCCGGGTTGT GGTCTGCGGT GACAGTTTCG GAGGGGCAAT
1001 AGCCGCAGTG GTTTGTCAAC AACTTGTGGA CAGGCCAGAT CTGCCCCGGA
1051 TCCGGGCTCA GATCCTGATC TATGCCATTC TCCAAGCCCT GGATTTACAA
1101 ACCCCTTCGT TTCAACAGAG GAAAAACATC CCACTGCTCA CCTGGAGTTT
1151 CATCTGCTAC TTTTTTTTC AAAACCTGGA TTTCAGCTCC TCCTGGCAAG
1201 AGGTCATCAT GAAAGGTGCC CATTTGCCTG CTGAAGTCTG GGAAAAGTAC
1251 AGAAAGTGGT TGGGCCCAGA AAACATCCCT GAGAGGTTTA AGGAGAGGGG
1301 TTACCAACTG AAGCCCCATG AGCCCATGAA TGAAGCTGCT TACTTGGAAG
1351 TAAGTGTTGT CCTGGATGTG ATGTGCTCGC CCCTGATTGC AGAAGATGAC
1401 ATAGTGTCTC AGCTCCCGGA AACCTGCATC GTGAGCTGTG AGTATGATGC
1451 TCTCCGGGAC AATTCACTGT TGTACAAGAA AAGGCTGGAA GACCTGGGAG
1501 TGCCCGTGAC CTGGCACCAT ATGGAGGATG GTTTCCATGG AGTGCTCAGG
1551 ACCATTGACA TGAGCTTCTT GCACTTTCCC TGCTCCATGA GAATTCTGAG
1601 TGCATTAGTT CAATTTGTAA AGGGACTGTG ACCATCTTTC TTCTCTGCTG
1651 GTACTGCGGT GTGGATTCCA CTGGCATCCA GCCTCCCACA GGGCTCTCTG
1701 TTGCTGATTT AGGTGGTGCA TAGTGGGGCT AGGGAGGGGG TAGAGGTTGC
1751 TGTCACCTTT CTGGTCCAGG TTCTAGAACC ACACAATGCA TGCTCCTGAT
1801 GTCCAGAGGA CGTGGTAGAA AAGACAGGTT TGGAGGTGGG AGTGTGGCTG
1851 TCTCTATTCT CTGTTGGGAA AACCTGGGCT GACAATATTC AGTGGCCATT
1901 TGTGGGAGTG AATCAGCCGG TAAGAGCTGT TCTCAGCCTC CCTAAGGGGC
1951 AGTTCAGGCT CCCAGATTGA TCCAGACTGT GTGTGACTTT CGTCCATTTG
2001 ACTTGACTTT GGAATAGCAC AAGGGCATCA TGTACTTCAC GAGGCTTTCC
2051 CAATGTGGCT CAGAGGCAGG AGCTCTGATG CTCTGGGCTG CTGTGAGGTG
2101 GTGGTGGTGG TAGAGAAACT GGCTTCACCC ACCTACTCTT CTGTGAACAG
2151 TAGTGACTTT TCCCGCTGTT TCTCAGCCTC TGGGATCAGA GTCTTCACTG
2201 TCTGGGCTGG AAACTTTAAG ATAGAATGGA TAGAGCTTCC ACAGTGGTTG
2251 GCATCTAGTG GTGGATGAAG ACAGCCTGCA GCTGCCCGAC TTGGGGAGCT
2301 CTGGAGCTCC TGGAATCAAA GCCTGTCTTC CAACCAGAAG CCCCAAGGCA
2351 ATGTTCTAAG AATTTGAGAA GAGAAGTTGG GAGGGAAGTG GGGTCCTGAG
2401 TTAGAGACCC ATGAAGGCTG AGTCTAACCA GATAACCCTG TCCACAGTGC
2451 AAAGTCAAGA CAGCCAAAGG AACAGAAGAT GTATTTGTGA AAACTATTTC
```

```
   1 GATTTTAGTC CCAGACAGCC GAGCCAGATC CGGGGCGAAC GCAAAGAACA
  51 GAGGGAGAAG GGGAGCAGGG AGGCGAGAGG AGGGCAGTAC ATGTAAGCCA
 101 GGTCAACAGA GGCACATCAC GGACTAAAGA AGCGGGACAG GCGGGGGAAG
 151 AAGAAGAAAA AGAAAGGGTA ACCCTAAAAC GAGAAGCGGC GGGAGGCGAC
 201 AAGCTTAAGA CCGGTACAGG ACGAGAAAAC CCAAGCAATA ATACCCCCCA
 251 GCAAAAAGGA GTATAGTTCC AGCGAAAGAG CGAAACGGAT ATCTACACGC
 301 CGGCGAACAC GACCACGGGA CGCAGAGAGC AAGGCAAAAG AAAAAAAAGG
 351 TGTAAAGAAG CAGGGGAGCG GACCTGGGAA GGGCGACAGA GAGGGGGAAG
 401 CAACCATAGA CGGCCTGGAC ATAAATGAGC CTGGCAACAG CAGCGCGCGT
 451 TCGCAGTAGA AGACCCTCTA TGGGTCGCGG GCAGGCAAGG GGTCGCTGTG
 501 CACATCCCTG CAGCGGTTGG CCACCCTGTG AAACTGAGAG TCCTCCATTG
 551 CATCTTCCAG CTGCTGTTGA CTTGGGGGAT GATATTTGAG AAGCTCAGAA
 601 TCTGTTCTAT GCCCCAATTT TTCTGTTTCA TGCAAGATCT GCCTCCGCTA
 651 AAGTATGACC CCGATGTTGT GGTCACGGAT TTCTGCTTTG GACAATCCC
 701 TGTGAAGCTG TACCAACCCA AGGCATCCAC CTGCACCCTG AAGCCTGGCA
 751 TCGTGTACTA CCACGGTGGC GGGGGCGTCA TGGGGAGTTT GAAAACCCAC
 801 CATGGCATAT GCTCTCGTTT GTGCAAGGAG AGTGACTCCG TGGTTCTGGC
 851 AGTTGGTTAC CGCAAGTTAC CTAAGCATAA GTTTCCAGTG CCAGTAAGAG
 901 ACTGCTTGGT GGCCACCATC CACTTCCTGA AGTCCCTGGA TGCATATGGA
 951 GTGGATCCAG CCCGGGTTGT GGTCTGCGGT GACAGTTTCG GAGGGGCAAT
1001 AGCCGCAGTG GTTTGTCAAC AACTTGTGGA CAGGCCAGAT CTGCCCCGGA
1051 TCCGGGCTCA GATCCTGATC TATGCCATTC TCCAAGCCCT GGATTTACAA
1101 ACCCCTTCGT TTCAACAGAG GAAAAACATC CCACTGCTCA CCTGGAGTTT
1151 CATCTGCTAC TTTTTTTTTC AAAACCTGGA TTTCAGCTCC TCCTGGCAAG
1201 AGGTCATCAT GAAAGGTGCC CATTTGCCTG CTGAAGTCTG GAAAAGTAC
1251 AGAAAGTGGT TGGGCCCAGA AAACATCCCT GAGAGGTTTA AGGAGAGGGG
1301 TTACCAACTG AAGCCCCATG AGCCCATGAA TGAAGCTGCT TACTTGGAAG
1351 TAAGTGTTGT CCTGGATGTG ATGTGCTCGC CCCTGATTGC AGAAGATGAC
1401 ATAGTGTCTC AGCTCCCGGA AACCTGCATC GTGAGCTGTG AGTATGATGC
1451 TCTCCGGGAC AATTCACTGT TGTACAAGAA AAGGCTGGAA GACCTGGGAG
1501 TGCCCGTGAC CTGGCACCAT ATGGAGGATG GTTTCCATGG AGTGCTCAGG
1551 ACCATTGACA TGAGCTTCTT GCACTTTCCC TGCTCCATGA GAATTCTGAG
1601 TGCATTAGTT CAATTTGTAA AGGGACTGTG ACCATCTTTC TTCTCTGCTG
1651 GTACTGCGGT GTGGATTCCA CTGGCATCCA GCCTCCCACA GGGCTCTCTG
1701 TTGCTGATTT AGGTGGTGCA TAGTGGGGCT AGGGAGGGGG TAGAGGTTGC
1751 TGTCACCTTT CTGGTCCAGG TTCTAGAACC ACACAATGCA TGCTCCTGAT
1801 GTCCAGAGGA CGTGGTAGAA AAGACAGGTT TGGAGGTGGG AGTGTGGCTG
1851 TCTCTATTCT CTGTTGGGAA AACCTGGGCT GACAATATTC AGTGGCCATT
1901 TGTGGGAGTG AATCAGCCGG TAAGAGCTGT TCTCAGCCTC CCTAAGGGGC
1951 AGTTCAGGCT CCCAGATTGA TCCAGACTGT GTGTGACTTT CGTCCATTTG
2001 ACTTGACTTT GGAATAGCAC AAGGGCATCA TGTACTTCAC GAGGCTTTCC
2051 CAATGTGGCT CAGAGGCAGG AGCTCTGATG CTCTGGGCTG CTGTGAGGTG
2101 GTGGTGGTGG TAGAGAAACT GGCTTCACCC ACCTACTCTT CTGTGAACAG
2151 TAGTGACTTT TCCCGCTGTT TCTCAGCCTC TGGGATCAGA GTCTTCACTG
2201 TCTGGGCTGG AAACTTTAAG ATAGAATGGA TAGAGCTTCC ACAGTGGTTA
2251 GCATCTAGTG GTGGATGAAG ACAGCCTGCA GCTGCCCGAC TTGGGGAGCT
2301 CTGGAGCTCC TGGAATCAAA GCCTGTCTTC CAACCAGAAG CCCCAAGGCA
2351 ATGTTCTAAG AATTTGAGAA GAGAAGTTGG GAGGGAAGTG GGGTCCTGAG
2401 TTAGAGACCC ATGAAGGCTG AGTCTAACCA GATAACCCTG TCCACAGTGC
2451 AAAGTCAAGA CAGCCAAAGG AACAGAAGAT GTATTTGTGA AAACTATTTC
```

FIG. 1A

2501 TTTTTTAAGA CATGGAACCA ACTCAAATTG GCCTCTATTA GAAAGACAAT
2551 AGATTGGCTT AGGTAGGGGT GCATGCTAGG CATACATCAG GCAAGGTTTG
2601 ATCCAGGAAC TCACACAGTG CCATCAGCTG TCCTGTCTTC TCTGCTCTGC
2651 TCTTCTCTCC TCTGTGTTAA TGCCACCTTC TCCTCTTCAT ACGGTGGCAC
2701 TGAGCAGCTT CATGCCTACC TTCCTCCAGG GTCAAGTTCA TTATCATGGA
2751 CTTGCCTCAT GCTCAGCAGT CCCAGAAAAA AGCCTAATTG CAACTTGATG
2801 GCTTTGTTGG CTTTCTGAGC AATGTGTCCA GTTGCCACAG TGAAGGGAAT
2851 GGAATAATCT AACTCACCAT TCCCAAGTCC TATGCCATCC TGAGAGTGGG
2901 GGGTGGAGTC AATTCACCTT GGTGCTTGGA CTAAGCATGA GGTGGTGAGT
2951 GACAACGTTC CTAATTGAAG GGTAGGGTAA ATGGTTGTTG GGTGGACACC
3001 AACACTTATT CTACTACAGA AGCTAAATTG AACCCTCAGG CAGGGTACGT
3051 GAAAGTGGCA AGAGATGTCA AGACCACTGG GCAAGTTGGC CAGTTGTTCC
3101 TTAGGAATGA AAATTCTTTT GAAAGGAATG GCCAGGGTCC TCTGCTGGCC
3151 CCACTTGGTC TTCTGGAGGC TCTGATCTTG GTTGGTTAGT GGTCTTTACA
3201 GGCCAAGGTC AAGGCCATTG CACAAAAAAC CCTGTGCATG CCCTTAACTT
3251 GCTTTCAGTT GAATATTTGG GCTGAACTAT GAGGCAGAGA GGAATCCCAT
3301 TGGGTGGCTC CTTGCTGCAT TCGCAGTTGA CCAGCATGGG GTTTGTTGGA
3351 GAAATAGGAA CCATCCCCTG AAAACACACA CTATGGTAGC CACTCAACTG
3401 TTGAAAGGCA CTGGAGTCCA ATGGGTGAGG CCGCCTCTGA GACAAGCCTC
3451 TGAGTTGAGG CTGGGAGAGG CTCCCTCCTT GGAGTGTTGC TTTTTTTGTT
3501 TCACCCCTGC CTCTGGAGAT GGGTAGAGGA ACATGAGCTG ACCTTCTGGG
3551 AAGTTAGGTT GGTGAGGAGT TGCTGAGGCA CTGCAGGGCC ATGCCCAGTA
3601 GAGAGGAATG TATAACATTT TAAGAGGCTG AGAGCACCCC TTGTTGGGCG
3651 CATGCCCATG GCAGCTTCCT TCTGCCGATC ATGGGAGAAA TCAAGCACTT
3701 TCACCTAATG GCTAGATGAT TGATTTTGGG ATGAAATTCT CCACTCCTCT
3751 CCTTTACCAC ATCACCACTA TCCTTCCTGC AATACATCCA CGAGACTCAC
3801 TGAGTGGAAA AGGGATAGGA ATGAATGTTC ACCCAGGGCC AGCTACATGC
3851 TAGGCACTGT ACTGGACCAT TTAAATTTGC CACCTCTTAT GTTCCTCACA
3901 TTAATCTTAC AGAGTAGGTA CAGACATACC TATGGATATT GCAGATTCAG
3951 TTCCAGACCA CAGCAATAAA GCAAGTCACA TGAATTTTTT GCTTTCCTTA
4001 GTGCATGTAA AAGTTACATT TCCACTATAT TATAGTTTAT TAAGTGTGCA
4051 ATAGCATTAT GTCTTTAAAA AGCATGTACA TACCTTAATT TAAAAATACC
4101 TTGTTGCTGA AAAATGCTAA CAATCATCTG AGCCTTCAGT GATTGCAGTA
4151 GCCTAGGCTA CTATTTTCTA TGTGGGGTTT GCACATTCTG CCCATGTCTG
4201 CGTGGGTTTT CTCTGAGTTC TCCAGCTTCC TCCCACATTC CAAAGATGTG
4251 TATGTTACAT TCATGGGAAT GTCTAAATTG TCGTAATCTT TTTGCTGGTT
4301 GATGGTCTTG CCTTGATGTT GATGCTGCAG GTGGTGGTTG CTGAAGGTGG
4351 GGGAGGCTGT GGCAATTTCT TAAAATAAAA TAAGACAACA GTGAAA
(SEQ ID NO: 1)

FEATURES:
5'UTR:        1 - 578
Start Codon:  579
Stop Codon:   1629
3'UTR:        1632

FIG.1B

Homologous proteins:
Top 10 BLAST Hits:

Sequences producing significant alignments:                              Score    E
                                                                         (bits)  Value CRA|1000682330001 /altid=gi|10120490 /def=ref|NP_065413.1| aryl...        206    2e-51
CRA|98000043615586 /altid=gi|12842312 /def=dbj|BAB25554.1| (AKO...        204    6e-51
CRA|157000140415711 /altid=gi|13184050 /def=ref|NP_075872.1| ar...        204    6e-51
CRA|88000001158504 /altid=gi|7513557 /def=pir||A58922 esterase/...        204    8e-51
CRA|18000004923710 /altid=gi|4557227 /def=ref|NP_001077.1| aryl...        196    1e-48
CRA|335001098689067 /altid=gi|11433103 /def=ref|XP_003002.1| ar...        196    1e-48
CRA|87000000006783 /altid=gi|7243107 /def=dbj|BAA92601.1| (AB03...        176    1e-42
CRA|18000005182547 /altid=gi|7499999 /def=pir||T21450 hypotheti...        139    2e-31
CRA|18000005176317 /altid=gi|7509799 /def=pir||T26848 hypotheti...        125    3e-27
CRA|18000005045863 /altid=gi|7499250 /def=pir||T25699 hypotheti...        101    6e-20

EXPRESSION INFORMATION FOR MODULATORY USE:
Tissue expression:
Placenta

FIG.1C

```
  1 MIFEKLRICS MPQFFCFMQD LPPLKYDPDV VVTDFCFGTI PVKLYQPKAS
 51 TCTLKPGIVY YHGGGGVMGS LKTHHGICSR LCKESDSVVL AVGYRKLPKH
101 KFPVPVRDCL VATIHFLKSL DAYGVDPARV VVCGDSFGGA IAAVVCQQLV
151 DRPDLPRIRA QILIYAILQA LDLQTPSFQQ RKNIPLLTWS FICYFFFQNL
201 DFSSSWQEVI MKGAHLPAEV WEKYRKWLGP ENIPERFKER GYQLKPHEPM
251 NEAAYLEVSV VLDVMCSPLI AEDDIVSQLP ETCIVSCEYD ALRDNSLLYK
301 KRLEDLGVPV TWHHMEDGFH GVLRTIDMSF LHFPCSMRIL SALVQFVKGL
(SEQ ID NO: 2)
```

FEATURES:
Functional domains and key regions:
[1] PDOC00005 PS00005 PKC_PHOSPHO_SITE
Protein kinase C phosphorylation site Number of matches: 3
    1    58-60 TLK 2    75-77 SLK 3    341-343 SMR

---

[2] PDOC00006 PS00006 CK2_PHOSPHO_SITE
Casein kinase II phosphorylation site 210-213 SWQE

---

[3] PDOC00007 PS00007 TYR_PHOSPHO_SITE
Tyrosine kinase phosphorylation site 241-247 RFKERGY

---

[4] PDOC00008 PS00008 MYRISTYL
N-myristoylation site

Number of matches: 8
    1    70-75 GGVMGS 2    71-76 GVMGSL 3    74-79 GSLKTH 4    129-134 GVDPAR 5    143-148 GGAIAA 6    144-149 GAIAAV 7    312-317 GVPVTW

FIG.2A 8    326-331 GVLRTI

Membrane spanning structure and domains:
 Helix Begin   End   Score Certainity
    1    53    73   0.627 Putative
    2   130   150   0.826 Putative
    3   182   202   1.214 Certain
    4   328   348   0.673 Putative BLAST Alignment to Top Hit:
CRA|1000682330001 /altid=gi|10120490 /def=ref|NP_065413.1|
         arylacetamide deacetylase [Rattus norvegicus] /org=Rattus
         norvegicus /taxon=10116 /dataset=nraa /length=398
      Length = 398

Score =  206 bits (519), Expect = 2e-51
 Identities = 124/360 (34%), Positives = 191/360 (52%), Gaps = 8/360 (2%)
 Frame = +3

Query:  492  VAVHIPAAVGHPVKLRVLHCIFQL---LLTWGMIFEKLRICSMPQFFCFMQDLPPLKYDP  662
             + + +P +   P K+ + + + +L       L  ++G +          Q F   Q +PP    D
Sbjct:   18  IYIPLPDDIEEPWKIILGNTLLKLGGDLASFGELLGLNHFMDTVQLFMRFQVVPPTS-DE   76

Query:  663  DVVVTDFCFGTIPVKLYQPKASTCTLKPGIVYYHGGGGVMGSLK--THHGICSRLCKESD  836
             +V V +    F  ++PV++Y PK   + TL+ G+ + HGGG  +GS      +   + R       D
Sbjct:   77  NVTVMETDFNSVPVRIYIPKRKSTTLRRGLFFIHGGGWCLGSAAYFMYDTLSRRTAHRLD  136

Query:  837  SVVLAVGYRKLPKHKFPVPVRDCLVATIHFLKS--LDAYGVDPARVVVCGDSFGGAIAAV 1010
             +VV++ + Y    PK+ FP     D  +     FL+    L+ YGVDP RV V GDS GG + A
Sbjct:  137  AVVVSTDYGLAPKYHFPKQFEDVYHSLRWFLQEDILEKYGVDPRRVGVSGDSAGGNLTAA  196

Query: 1011  VCQQLVDRPDLP-RIRAQILIYAILQALDLQTPSFQQRKNIPLLTWSFICYFFFQNLDFS 1187
             V QQ++   PD+   +++  Q LIY   LQALD+  PS Q+       PLLT S + F+ +
Sbjct:  197  VTQQILQDPDVKIKLKVQALIYPALQALDMNVPSQQENSQYPLLTRSLLIRFWSEYFTTD  256

Query: 1188  SSWQEVIMKGAHLPAEVWEKYRKWLGPENIPERFKERGYQLKPHEPMNEAAYLEVSVVLD 1367
             ++  ++    H+P E        +    +P+R+K +GY  K  P  +           D
Sbjct:  257  RDLEKAMLLNQHVPVEFSHLLQFVNWSSLLPQRYK-KGYFYKTPTPGSLELAQKYPGFTD  315

Query: 1368  VMCSPLIAEDDIVSQLPETCIVSCEYDALRDNSLLYKKRLEDLGVPVTWHHMEDGFHGVL 1547
             V    PL+A D I+   LP T I++C+YD LRD+  L+Y KRL++  GV VT HH+EDGFHG L
Sbjct:  316  VKACPLLANDSILHHLPMTYIITCQYDVLRDDGLMYVKRLQNTGVHVTHHHIEDGFHGAL  375
      (SEQ ID NO: 4)

FIG.2B

CRA|98000043615586 /altid=gi|12842312 /def=dbj|BAB25554.1| (AK008244)
            putative [Mus musculus] /org=Mus musculus /taxon=10090
            /dataset=nraa /length=341
         Length = 341

Score =  204 bits (514), Expect = 7e-51
 Identities = 117/314 (37%), Positives = 175/314 (55%), Gaps = 5/314 (1%)
 Frame = +3

```
Query: 615   QFFCFMQDLPPLKYDPDVVVTDFCFGTIPVKLYQPKASTCTLKPGIVYYHGGGGVMGSLK 794
             Q    Q++PP  D V V + F ++PV++Y PK  + L+ G+ Y HGGG +GS
Sbjct: 5     QLLMSFQEVPPTS-DEHVTVMETAFDSVPVRIYIPKRKSMALRRGLFYIHGGGWCLGSAA 63

Query: 795   --THHGICSRLCKESDSVVLAVGYRKLPKHKFPVPVRDCLVATIHFLKS--LDAYGVDPA 962
               ++   +        + D+VV++  Y   PKH FP   D   FL+   L+ YGVDP
Sbjct: 64    HFSYDTLSRWTAHKLDAVVVSTDYGLAPKHHFPRQFEDVYRSLRWFLQEDVLEKYGVDPR 123

Query: 963   RVVVCGDSFGGAIAAVVCQQLVDRPDLP-RIRAQILIYAILQALDLQTPSFQQRKNIPLL 1139
             RV V GDS GG +AA V QQL+  PD+   +++ Q LIY  LQALD   PS Q+  + P+L
Sbjct: 124   RVGVSGDSAGGNLAAAVTQQLIQDPDVKIKLKVQALIYPALQALDTNVPSQQEGSHFPVL 183

Query: 1140  TWSFICYFFFQNLDFSSSWQEVIMKGAHLPAEVWEKYRKWLGPENIPERFKERGYQLKPH 1319
             T S + F++      ++  ++ ++  H+P E  +     +PER+K+       P
Sbjct: 184   TRSLMVRFWSEYFTTDRGLEKAMLLNQHVPMESSHLLQFVNWSSLLPERYKKSPVYKNPT 243

Query: 1320  EPMNEAAYLEVSVVLDVMCSPLIAEDDIVSQLPETCIVSCEYDALRDNSLLYKKRLEDLG 1499
             +E A  +   +DV   PL+A D+I+  LP+T I++C+YD LRD+  L+Y KRL+++G
Sbjct: 244   PGSSELAQ-KYPGFIDVKACPLLANDNILHHLPKTYIITCQYDVLRDDGLMYVKRLQNVG 302

Query: 1500  VPVTWHHMEDGFHG 1541
             V VT HH+EDGFHG
Sbjct: 303   VHVTHHHVEDGFHG 316 (SEQ ID NO: 5)
```

Hmmer search results (Pfam):
Scores for sequence family classification (score includes all domains):

| Model | Description | Score | E-value | N |
|---|---|---|---|---|
| PF00530 | Scavenger receptor cysteine-rich domain | 6.3 | 2.1 | 1 |
| PF00702 | haloacid dehalogenase-like hydrolase | 2.9 | 7.2 | 1 |
| PF00798 | Arenavirus glycoprotein | 1.7 | 2 | 1 |

Parsed for domains:

| Model | Domain | seq-f | seq-t | hmm-f | hmm-t | score | E-value |
|---|---|---|---|---|---|---|---|
| PF00798 | 1/1 | 11 | 22 .. | 1 | 12 [. | 1.7 | 2 |
| PF00702 | 1/1 | 116 | 143 .. | 142 | 173 .. | 2.9 | 7.2 |
| PF00530 | 1/1 | 131 | 149 .. | 22 | 46 .. | 6.3 | 2.1 |

FIG.2C

```
   1 GGGTCACTCT GTGGGTCATT TGCAGCCTTT TTTCACTGTG CACATCCCTG
  51 CAGCGGTTGG CCACCCTGTG AAACTGAGAA GTCCTCCATT GCATCTTCCA
 101 GCTGCTGTTG ACTTGGGTGA GTTTTGTGCT TTATGTGTCC CCTCCAGCTG
 151 ACCATTAAGG AAGGCGGCAG GAAAAATCAC ACACCGGAAG CTTCTAGCTG
 201 AATGAACACC GGTATCATGG GGCCTGCAGT GACAGCTGAT CAGACCTTCT
 251 GAAATGTGCA TAATCCCTAT TAGGTGGTTC TCAGCCTCTT TGGGTGTTTC
 301 TGAAGCTGGC CCTGGCTAAT ATTCACAAAA TTCAAAGAAT GATCTGCTTT
 351 CTCAGTTAAC AGAAAGAAAA AACCAGTCTG GTTCTATTCA CCTGAGTGTC
 401 TCCCGCTGAC TTTCTTTTTG TTGTTGTTGG TTTGTTTTAT TTTTAAAATT
 451 GAGGTAAAAT ATGCATATAA AATTTACCAT CTTTCGCATT TTTAAGTGTA
 501 CCTTTCACGT GTCCATAAAT GTGTCCATAT TATTCACAGC ACTCACCACT
 551 CTCAGAAGTT GTGAAGATAT GAATGAATTT TCCTGAGTCT CTGGGCCCCC
 601 ACTGCTATCT ACCTGTTAGC TAGAGCCAGC AAGCCACAAA GTAAAAGGGT
 651 AGCGGATGAG TAGATTAGTG CCGGTGAGCA AAATTACAGA ATGTGACTTT
 701 AAAAATATGT TGTTGCTTTT GAGAGCTAGA AAGCTGCCTA GGGAATATAG
 751 TTTGGTTCTG CTTCTGGTGT AATTTGTTAA AATACCTGTA AATGGAACTG
 801 TGTAGGTGTT GCCCAATACG GATTTCTTGT ACTTTTTCTT GTGCCTTGAC
 851 AGAAACTGAA TATACAAAAT ATTTTTTGTA AGTTTCTTAC ATAACGAAAA
 901 GCAATTGCCA GTGCCTCTTC TCAAGAGACA CCCTAGGTGT GTCTTCTATG
 951 CTATTCAAAA TAATTTCTAT GCTATTCAAA AGAATGTAGC TATTACCTAA
1001 AAGAGAAGAT CCCGGGAACT CTAGGCTTCT GATCTCCAGT CAGCTTTTAT
1051 AAGATGCAGT GATTGGGTCC TAGGTTTTCC TACCCTTGAT GCTCAGATTC
1101 TGTAGTCCAG GCTCCCAAAT ACAGTGACTC AATTTCCTCT TTTGCAAAGT
1151 AGGGAAAATT GCTCCTACTT CACAGGGTTT TGTGGAGACT CCATGAATAA
1201 CCCTCTCCAG AAGGCTTATT ATAATGCCTG ACACAGAGGG AGCCCTCCTT
1251 AAATAGTAGC CATTGTTACT CTTTGTTGAT TCTTTTATTT TTTATGCAAA
1301 GATGTGTTAT GCAACTGCTG TGTGTCCTAC GCCAGTCCTG GGCTCTAGGG
1351 CCAATGACAG GTGAGAGAGG TAAAGTTCCA CAGGTCTGCC TTTAGGGAGC
1401 TTGTAGGGTC CAGGCAGTGG GCAGCGGGGA AGTGGTCTAT AAAGAAGCTA
1451 ACCCACAATA GAACAAGCTA CAGATAAACA GCTTCCCAAA GCGGAGAATG
1501 CAAGGAGGAC AGCAAAACCC GTCAGGGGAG CCGAGCAGGG CTTCTCTCCT
1551 GGGGCATCTT GAGCCCCCGG GGCCACAGAA CACAAGGGGG TCATGGATTT
1601 GGATCACAGA ACATAAGGGG GTCATGGATT TGGGTCACAG AACACAAGGG
1651 GGTCATGGAT TTGGATGGGG TCAAAATTAC CCCATGTTCA CAACTAACTT
1701 CCAATTGAAA TTCTTCTCAT GAGGAATGAA GGCAACAAAC CACAGTCCTG
1751 AAAGCCAGAC CTCGACTTTT CACCAAGAGA AATCAGACAT ATTTGCATTG
1801 CCTATTAGAT ATTGCGAAAA CTCATGTATT CTCCTCATTT CTTTGAAACT
1851 AGGGTAGTAT CAGGCAGCAG TTAGATCTTA TTACTCTATG TGCTAGTAAG
1901 GAAGAACCTA TATTATTATG ACATACATTT TAATATTTTG ATAAGTATAT
1951 TTAAATAACA CTGCTTTTCT TTATAATCCC ATGTATTTAT TTTATGTATT
2001 TAAAAATGTT CTGGGCTGGG TGTAGTGGCT TACACCTGTA ATCCCAGCAC
2051 TTTGGGAGGC TGAGGTGGGA GGACTGTTTG AGTCCAGGAG TTTGAGACCA
2101 GCCTGGGTGA CATAATGAGG CCTCTTCTCT CCTAAAAAAA AAAAAAAAAA
2151 AAAAAGTTCT CAAATGAGGC CTGCAGCTTT TCCCAAGGCC AAAATGGCTG
2201 TGGCACAGAC AAGGATTAGG AAACACTGGA AAGGATACCC AGAGGGAGAG
2251 CCCTCTTTAT TTACGTATTT TTAACTCTTT TTTTTTGAGC TGGAGTTTTA
2301 CTCTTGTTGC CCAGGCTGGA GTGCAATGGC ATGATCTCGG CTTACTGCAA
2351 CCTCTGCCTC TAGGGTTCAA GAGATTCTTC TGCCTCAGCC TCTCGAGTAG
2401 CCGGGAATAC AGGAGCCCAC CACCACACCC ACCCGGCTAA TTTTTTGTATT
2451 TTCAGTAGAG ACTGGGTTTC ACCATGTTGG CCAGGCTGGC CTTGAACTCC
```

FIG.3A

```
2501 TGACCTCAAG TGACCCACCA GCCTTGGCCT CCCAAAGTGC TGGGATTACA
2551 GGTATCAGCC ACTGTGCCTG GCTGTATTTT CAACCCTTTA TGCAAACTTT
2601 GACATATACC AAAGGGGAAC AGGGTGCCCA CTCTCCAGTG TCACCATCAC
2651 TGACTCCTGG CCTGTCTCCC TTCCCTGTGT CCCTAAATGT CTCTAACTTT
2701 TCCCTCATTT TCATTTATTT AAGAAGCCAA TGGACATCAT ATTATTTTAT
2751 CCTAAAAATT TTCAGTAGGC ATTTTCAAAA GATATGAACT CCCCCTTCCT
2801 GTTTTTAAAA AATGTACCCA CACTATAGTT AGCTACACAG GCTTGGGGTG
2851 GCCAGATTGG CTGGGACGGC ACAGGAAGGC CTCCCTGGAA ACAGATGTTG
2901 CGCCCAGGCT GAGGTGGAGC AGGGCCTCGT GGTGGAGGTG GGTGTTGCAA
2951 GTAGAGGGAC CATCAAGGGT GCCCAGAAGC CTGGCTTGTA GTGGCTGCAG
3001 TGGAAGGTGT CAGGAGAGTG GGTTGAGAGG GGCTGGCTGG TGCTGTGGCC
3051 ACCTGGGCCT GCATGGGAGT GGATTTTCCT GCAGGTGTCC TGAGGGAACT
3101 GAGGGCTTGA GTAGGGCTGT AATCCAATCT GACTGCAGTT TCCAAAAACT
3151 CCTTTTGCCA CCTGTGGAGG GCAGGTTGTG AAGGCCAGAC TCCAGATGGC
3201 CTGTGAAGAA ACCCATCTCG ACCCATCATT TCTTCTCTCT CCAACAGGGG
3251 ATGATATTTG AGAAGCTCAG AATCTGTTCT ATGCCCCAAT TTTTCTGTTT
3301 CATGCAAGAT CTGCCTCCGC TAAAGTATGA CCCCGATGTT GTGGTCACGG
3351 ATTTCCGCTT TGGGACAATC CCTGTGAAGC TGTACCAACC CAAGGCATCC
3401 ACCTGCACCC TGAAGCCTGG CATCGTGTAC TACCACGGTG GCGGGGGCGT
3451 CATGGGGAGT TTGAGTAAGA ACCATTTTCT CAGACCTCCT AAAGGGTGGT
3501 GGCACCCCTT AACATAACTT GGAAGAATGG GCATCTTCCT GGGACTTAAA
3551 GTATGCTATT ATTATCAGGG AACACCAGGG CAGTTCATGG TTTGCAGATC
3601 ATTGAGGGGG CAAAAATATG GCATATATTG CCCTCTTATG TATCTCCTTA
3651 TTTACATAAA TGTAATCCTT AGTTAAATTA ACAATACTGT AATATAAGGA
3701 AGGATACTGT AAGGTAAAGA TCCTGAAATG TACCCTTACT TGCATTTATA
3751 TGTGTACATA TGTATGTACA TATAAATGTA TACATGTATA TTTCACTATT
3801 TTACTTATAA TCACCACCTC TATTTAGTTG GAAATAAGGA TATTTTAAAT
3851 GAAAAGAATT AAAACACAGC ATTTTGTTTC ACATCAGGTT TTGCTAAGAC
3901 AAATTCTGGT ACAGACAGAC AGGAAGATTT GAGAAAAATC AATGAGAGGA
3951 AAAAGTCACT ATTGAGACAA TTTTACTGTC TTAGTTATTA CCCCCAGGGA
4001 ATTAGGGGAG AGGAAACACC TTTATTTGCT TTCAGTAGTG CTTTCTAATC
4051 TGTGGAATGC CAGGGTCCCA GTGTGGGAGC CTTTGAGAAT AAAGGATTTA
4101 ATGCAATGGT GGTGTGGTTT GGTCTGTATG AGAATGATAG TAACAGCCAA
4151 TATTTATTAA GCAATATTCA TTAATATTAC TAATTACATG CAGGCACTGT
4201 GAGAACCCTA TATGTGGATG ATCTCATTCC AACTCCAACA CTCTACGAGT
4251 TAGATATTTT CATTACCCCA GTTCACAGAT GAGGAAATCA AGCCTCAGGA
4301 GGTTAAGAGA CTTGCTAGGC ACTATGTTAG CTCAAGCTAG AAAGGGGCAA
4351 AGTTGAGATT TGAACTCCAG TCTGAATCCA GAGCTCACAC CCTAAACCTC
4401 TGCGTTCTAC AGTCAAAGAG CTTCACAGAT ATTTTTAATG GCTTGTAGGA
4451 TGGATTGGAG GGTGGGCGTC TTAGAGAAAG TTGTTCAGGC AGTACCACGA
4501 AGGAGAATCA GTGAGAAGAT TGACCGGAAG TTTGCTGGAG TAGAGGAAAA
4551 CCTAGTCGGC ATCGGCCCAA GTGCTGTGTC TGTAGGAAGA AGACGGTGAC
4601 AATGGCTGGC AAAGGAAGCC TTCCTAGTGA ATCTTAAAAA CCATTTATTT
4651 TCTAGAAACC CACCATGGCA TATGCTCTCG TTTGTGCAAG GAGAGTGACT
4701 CCGTGGTTCT GGCAGTTGGG TGAGTAAAGG GGAGATCCCA GGGAGCCAGC
4751 AAGGAGCAAG GCTCTGATGT GGAGAGATGG GGTGAGAAGT AGAAATGGGG
4801 GTGGGGGGTG GGGGATGGGA GCAGATGGGA GCTGGAGGAA GCCCAGAGGT
4851 GGGGATGGGC TGGGAGAAGC CAGTGAAGAG AGAAAAAGAA GGCGGCTGGG
4901 TGTGGTGGCT CACGCCTGTA ATCCCAACAC TTTGGGAGGC CACGGTGGGC
4951 AGAATGCTTG AGCCCAGGAG TTCAGACCAG CCTGGGCAAC ATAGTGAGAC
```

FIG.3B

```
5001 CCCATTTTTA CAAAAAATAC AAAAATTAGC CAGGTGTGGT GGCATATGTC
5051 TGTAGTCCCA GCTACTTGGG AGGCCGAGGA GGAAGAAGCA CCTGAGCCTG
5101 GGAGGTTGCA GTGAGCCGTG ATTGCGCCAC TACACTCAGC CTGGGTGACA
5151 GAACAAGACC CTGTCTTAAA ACAAACAAAA CAAAACAAGA AAAAGAGAGT
5201 GAAAGAAAAA TAAGGGGAGG TGAAGAGAGA TGGAGAGACA GAGAATGGGG
5251 AACCCCTTCC TCTGTGCATG TGGGCCTTGG GTTTGTTTAA ACAGAGGCGT
5301 TTTGTGCATT TTGAAGCTGG GTAGGAGGTG GTCTTTTTTA AGCAGTTCAG
5351 GTGCAGAGTT TCACTGCAGG AACACTTGGA CAACATAGCT CTTCTTTGAG
5401 TAAAACAACC CTGCACCTCC TTCTGCTAAA TGCCTGTGGT ACCCCGCACC
5451 ATCACTCAAA CAACCCGAAA TGCTGCCACG TTCACTTCCA AGTGCTCCCA
5501 AAAGGGAGGT CCCCCTGGCT GAGACCCACT GAAGAAAGTG AGAAAAACAA
5551 AAACAAAAAC AAACCCATTG TCTCTCCTAA CAGATCTCTG ACAGTCACCG
5601 CCCAGCCTGG AGCCTCAAAG AGGGCGTGNN NNNNNNNNNN NNNNNNNNNN
5651 NNNNNNNNNN NNNNNNNNNN NNNNNNNNNN NNNNNNNNNN NNNNNNNNNN
5701 NNNNNNNNNN NNNNNNNNNN NNNNNNNNNN NNNNNNNNNN NNNNNNNNNN
5751 NNNNNNNNNN NNNNNNNNNN NNNNNNNNNN NNNNNNNNNN NNNNNNNNNN
5801 NNNNNNNNNN NNNNNNNNNN NNNNNNNNNN NNNNNNNNNN NNNNNNNNNN
5851 NNNNNNNNNN NNNNNNNNNN NNNNNNNNNN NNNNNNNNNN NNNNNNNNNN
5901 NNNNNNNNNN NNNNNNNNNN NNNNNNNNNN NNNNNNNNNN NNNNNNNNNN
5951 NNNNNNNNNN NNNNNNNNNN NNNNNNNNNN NNNNNNNNNN NNNNNNNNNN
6001 NNNNNNNNNN NNNNNNNNNN NNNNNNNNNN NNNNNNNNNN NNNNNNNNNN
6051 NNNNNNNNNN NNNNNNNNNN NNNNNNNNNN NNNNNNNNNN NNNNNNNNNN
6101 NNNNNNNNNN NNNNNNNNNN NNNNNNNNNN NNNNNNNNNN NNNNNNNNNN
6151 NNNNNNNNNN NNNNNNNNNN NNNNNNNNNN NNNNNNNNNN NNNNNNNNNN
6201 NNNNNNNNNN NNNNNNNNNN NNNNNNNNNN NNNNNNNNNN NNNNNNNNNN
6251 NNNNNNNNNN NNNNNNNNNN NNNNNNNNNN NNNNNNNNNN NNNNNNNNNN
6301 NNNNNNNNNN NNNNNNNNNN NNNNNNNNNN NNNNNNNNNN NNNNNNNNNN
6351 NNNNNNNNNN NNNNNNNNNN NNNNNNNNNN NNNNNNNNNN NNNNNNNNNN
6401 NNNNNNNNNN NNNNNNNNNN NNNNNNNNNN NNNNNNNNNN NNNNNNNNNN
6451 NNNNNNNNNN NNNNNNNNNN NNNNNNNNNN NNNNNNNNNN NNNNNNNNNN
6501 NNNNNNNNNN NNNNNNNNNN NNNNNNNNNN NNNNNNNNNN NNNNNNNNNN
6551 NNNNNNNNNN NNNNNNNNNN NNNNNNNNNN NNNNNNNNNN NNNNNNNNNN
6601 NNNNNNNNNN NNNNNNNNNN NNNNNNNNNN NNNNNNNNNN NNNNNNNNNN
6651 NNNNNNNNNN NNNNNNNNNN NNNNNNNNNN NNNNNNNNNN NNNNNNNNNN
6701 NNNNNNNNNN NNNNNNNNNN NNNNNNNNNN NNNNNNNNNN NNNNNNNNNN
6751 NNNNNNNNNN NNNNNNNNNN NNNNNNNNNN NNNNNNNNNN NNNNNNNNNN
6801 NNNNNNNNNN NNNNNNNNNN NNNNNNNNNN NNNNNNNNNN NNNNNNNNNN
6851 NNNNNNNNNN NNNNNNNNNN NNNNNNNNNN NNNNNNNNNN NNNNNNNNNN
6901 NNNNNNNNNN NNNNNNNNNN NNNNNNNNNN NNNNNNNNNN NNNNNNNNNN
6951 NNNNNNNNNN NNNNNNNNNN NNNNNNNNNN NNNNNNNNNN NNNNNNNNNN
7001 NNNNNNNNNN NNNNNNNNNN NNNNNNNNNN NNNNNNNNNN NNNNNNNNNN
7051 NNNNNNNNNN NNNNNNNNNN NNNNNNNNNN NNNNNNNNNN NNNNNNNNNN
7101 NNNNNNNNNN NNNNNNNNNN NNNNNNNNNN NNNNNNNNNN NNNNNNNNNN
7151 NNNNNNNNNN NNNNNNNNNN NNNNNNNNNN NNNNNNNNNN NNNNNNNNNN
7201 NNNNNNNNNN NNNNNNNNNN NNNNNNNNNN NNNNNNNNNN NNNNNNNNNN
7251 NNNNNNNNNN NNNNNNNNNN NNNNNNNNNN NNNNNNNNNN NNNNNNNNNN
7301 NNNNNNNNNN NNNNNNNNNN NNNNNNNNNN NNNNNNNNNN NNNNNNNNNN
7351 NNNNNNNNNN NNNNNNNNNN NNNNNNNNNN NNNNNNNNNN NNNNNNNNNN
7401 NNNNNNNNNN NNNNNNNNNN NNNNNNNNNN NNNNNNNNNN NNNNNNNNNN
7451 NNNNNNNNNN NNNNNNNNNN NNNNNNNNNN NNNNNNNNNN NNNNNNNNNN
```

FIG.3C

```
7501 NNNNNNNNNN NNNNNNNNNN NNNNNNNNNN NNNNNNNNNN NNNNNNNNNN
7551 NNNNNNNNNN NNNNNNNNNN NNNNNNNNNN NNNNNNNNNN NNNNNNNNNN
7601 NNNNNNNNNN NNNNNNNNNN NNNNNNNNNN NNNNNNNNNN NNNNNNNNNN
7651 NNNNNNNNNN NNNNNNNNNN NNNNNNNNNN NNNNNNNNNN NNNNNNNNNN
7701 NNNNNNNNNN NNNNNNNNNN NNNNNNNNNN NNNNNNNNNN NNNNNNNNNN
7751 NNNNNNNNNN NNNNNNNNNN NNNNNNNNNN NNNNNNNNNN NNNNNNNNNN
7801 NNNNNNNNNN NNNNNNNNNN NNNNNNNNNN NNNNNNNNNN NNNNNNNNNN
7851 NNNNNNNNNN NNNNNNNNNN NNNNNNNNNN NNNNNNNNNN NNNNNNNNNN
7901 NNNNNNNNNN NNNNNNNNNN NNNNNNNNNN NNNNNNNNNN NNNNNNNNNN
7951 NNNNNNNNNN NNNNNNNNNN NNNNNNNNNN NNNNNNNNNN NNNNNNNNNN
8001 NNNNNNNNNN NNNNNNNNNN NNNNNNNNNN NNNNNNNNNN NNNNNNNNNN
8051 NNNNNNNNNN NNNNNNNNNN NNNNNNNNNN NNNNNNNNNN NNNNNNNNNN
8101 NNNNNNNNNN NNNNNNNNNN NNNNNNNNNN NNNNNNNNNN NNNNNNNNNN
8151 NNNNNNNNNN NNNNNNNNNN NNNNNNNNNN NNNNNNNNNN NNNNNNNNNN
8201 NNNNNNNNNN NNNNNNNNNN NNNNNNNNNN NNNNNNNNNN NNNNNNNNNN
8251 NNNNNNNNNN NNNNNNNNNN NNNNNNNNNN NNNNNNNNNN NNNNNNNNNN
8301 NNNNNNNNNN NNNNNNNNNN NNNNNNNNNN NNNNNNNNNN NNNNNNNNNN
8351 NNNNNNNNNN NNNNNNNNNN NNNNNNNNNN NNNNNNNNNN NNNNNNNNNN
8401 NNNNNNNNNN NNNNNNNNNN NNNNNNNNNN NNNNNNNNNN NNNNNNNNNN
8451 NNNNNNNNNN NNNNNNNNNN NNNNNNNNNN NNNNNNNNNN NNNNNNNNNN
8501 NNNNNNNNNN NNNNNNNNNN NNNNNNNNNN NNNNNNNNNN NNNNNNNNNN
8551 NNNNNNNNNN NNNNNNNNNN NNNNNNNNNN NNNNNNNNNN NNNNNNNNNN
8601 NNNNNNNNNN NNNNNNNNNN NNNNNNNNNN NNNNNNNNNN NNNNNNNNNN
8651 NNNNNNNNNN NNNNNNNNNN NNNNNNNNNN NNNNNNNNNN NNNNNNNNNN
8701 NNNNNNNNNN NNNNNNNNNN NNNNNNNNNN NNNNNNNNNN NNNNNNNNNN
8751 NNNNNNNNNN NNNNNNNNNN NNNNNNNNNN NNNNNNNNNN NNNNNNNNNN
8801 NNNNNNNNNN NNNNNNNNNN NNNNNNNNNN NNNNNNNNNN NNNNNNNNNN
8851 NNNNNNNNNN NNNNNNNNNN NNNNNNNNNN NNNNNNNNNN NNNNNNNNNN
8901 NNNNNNNNNN NNNNNNNNNN NNNNNNNNNN NNNNNNNNNN NNNNNNNNNN
8951 NNNNNNNNNN NNNNNNNNNN NNNNNNNNNN NNNNNNNNNN NNNNNNNNNN
9001 NNNNNNNNNN NNNNNNNNNN NNNNNNNNNN NNNNNNNNNN NNNNNNNNNN
9051 NNNNNNNNNN NNNNNNNNNN NNNNNNNNNN NNNNNNNNNN NNNNNNNNNN
9101 NNNNNNNNNN NNNNNNNNNN NNNNNNNNNN NNNNNNNNNN NNNNNNNNNN
9151 NNNNNNNNNN NNNNNNNNNN NNNNNNNNNN NNNNNNNNNN NNNNNNNNNN
9201 NNNNNNNNNN NNNNNNNNNN NNNNNNNNNN NNNNNNNNNN NNNNNNNNNN
9251 NNNNNNNNNN NNNNNNNNNN NNNNNNNNNN NNNNNNNNNN NNNNNNNNNN
9301 NNNNNNNNNN NNNNNNNNNN NNNNNNNNNN NNNNNNNNNN NNNNNNNNNN
9351 NNNNNNNNNN NNNNNNNNNN NNNNNNNNNN NNNNNNNNNN NNNNNNNNNN
9401 NNNNNNNNNN NNNNNNNNNN NNNNNNNNNN NNNNNNNNNN NNNNNNNNNN
9451 NNNNNNNNNN NNNNNNNNNN NNNNNNNNNN NNNNNNNNNN NNNNNNNNNN
9501 NNNNNNNNNN NNNNNNNNNN NNNNNNNNNN NNNNNNNNNN NNNNNNNNNN
9551 NNNNNNNNNN NNNNNNNNNN NNNNNNNNNN NNNNNNNNNN NNNNNNNNNN
9601 NNNNNNNNNN NNNNNNNNNN NNNNNNNNNN NNNNNNNNNN NNNNNNNNNN
9651 NNNNNNNNNN NNNNNNNNNN NNNNNNNNNN NNNNNNNNNN NNNNNNNNNN
9701 NNNNNNNNNN NNNNNNNNNN NNNNNNNNNN NNNNNNNNNN NNNNNNNNNN
9751 NNNNNNNNNN NNNNNNNNNN NNNNNNNNNN NNNNNNNNNN NNNNNNNNNN
9801 NNNNNNNNNN NNNNNNNNNN NNNNNNNNNN NNNNNNNNNN NNNNNNNNNN
9851 NNNNNNNNNN NNNNNNNNNN NNNNNNNNNN NNNNNNNNNN NNNNNNNNNN
9901 NNNNNNNNNN NNNNNNNNNN NNNNNNNNNN NNNNNNNNNN NNNNNNNNNN
9951 NNNNNNNNNN NNNNNNNNNN NNNNNNNNNN NNNNNNNNNN NNNNNNNNNN
```

FIG.3D

```
10001 NNNNNNNNNN NNNNNNNNNN NNNNNNNNNN NNNNNNNNNN NNNNNNNNNN
10051 NNNNNNNNNN NNNNNNNNNN NNNNNNNNNN NNNNNNNNNN NNNNNNNNNN
10101 NNNNNNNNNN NNNNNNNNNN NNNNNNNNNN NNNNNNNNNN ACACAATGCA
10151 TGCTCCTGAT GTCCAGAGGA CGTGGTAGAA AAGACAGGTT TGGAGGTGGG
10201 AGTGTGGCTG TCTCTATTCT CTGTTGGGAA AACCTGGGCT GACAATATTC
10251 AGTGGCCATT TGTGGGAGTG AATCAGCCGG TAAGAGCTGT TCTCAGCCTC
10301 TCTAAGGGGC AGTTCAGGCT CCCAGATTGA TCCAGACTGT GTGTGACTTT
10351 TGTCCATTTG ACTTGACTTT GGAATAGCAC AAGGGCATCA CGTACTTCAC
10401 GAGGCTTTCC CAATGTGGCT CAGAGGCAGG AGCTCTGATG CTCTAGGCTG
10451 CTGTGAGGTG GTGGTGGTGG TGGAGAAACT GGCTTCACCC ACCTACTCTT
10501 CTGTGAACAG TAGTGACTTT TCCCGCTGTT TCTCAGCCTC TGGGATCAGA
10551 GTCTTCACTG TCTGGGCTGG AAACTTTAAG ATAGAATGGA TAGAGCTTCC
10601 ACAGTGGTTG GCATCTAGTG GTGGATGAAG ACAGCCTGCA GCTGCCCGAC
10651 TTGGGGAGCT CTGGAGCTCC TGGAATCAAA GCCTGTCTTC CAACCAGAAG
10701 CCCCAAGGCA ATGTTCTAAG AATTTGAGAA GAGAAGTTGG GAGGGAAGTG
10751 GGGTCCTGAG TTAGAGACCC ATGAAGGCTG AGTCTAACCA GATAACCCTG
10801 TCCACAGTGC AAAGTCAAGA CAGCCAAAGG AACAGAAGAT GTATTTGTGA
10851 AAACTATTTC TTTTTTAAGA CATGGAACCA ACTCAAATTG GCCTCTATTA
10901 GAAAGACAAT AGATTGGCTT AGGTAGGGAT GCATGCTAGG CATACATCAG
10951 GCAAGGTTTG ATCCAGGAAC TCACACAGTG CCATCAGCTG TCCTGTCTTC
11001 TCTGCTCTGC TCTTCTCTCC TCTGTGTTAA TGCCACCTTC TCCTCTTCAT
11051 ACGGTGGCAC TGAGCAGCTT CATGCCTACC TTCCTCCAGG GTCAAGTTCA
11101 TTATCATGGA CTTGCCTCAT GCTCAGCAGT CCCAGAAAAA AGCCTAATTG
11151 CAACTTGATG GCTTTGTTGG CTTTCTGAGC AATGTGTCCA GTTGCCACAG
11201 TGAAGGGAAT GGAATAATCT AACTCACCAT TCCCAAGTCC TATGCCATCC
11251 TGAGAGTGGG GGGTGGAGTC AATTCACCTT GGTGCTTGGA CTAAGCATGA
11301 GGTGGTGAGT GACAACGTTC CTAATTGAAG GGTAGGGTAA ATGGTTGTTG
11351 GGTGGACACC AACACTTATT CTACTACAGA AGCTAAATTG AACCCTCAGG
11401 CAGGGTACGT GAAAGTGGCA AGAGATGTCA AGACCACTGG GCAAGTTGGC
11451 CAGTTGTTCC TTAGGAATGA AAATTCTTTT GAAAGGAATG CCAGGGTCC
11501 TCTGCTGGCC CCACTTGGTC TTCTGGAGGC TCTGATCTTG GTTGGTTAGT
11551 GGTCTTTACA GGCCAAGGTC AAGGCCATTG CACAAAAAAC CCTGTGCATG
11601 CCCTTAACTT GCTTTCAGTT GAATATTTGG GCTGAACTAT GAGGCAGAGA
11651 GGAATCCCAT TGGGTGGCTC CTTGCTGCAT TCGCAGTTGA CCAGCATGGG
11701 GTTTGTTGGA GAAATAGGAA CCATCCCCTG AAAACACACA CTATGGTAGC
11751 CACTCAACTG TTGAAAGGCA CTGGAGTCCA ATGGGTGAGG CCGCCTCTGA
11801 GACAAGCCTC TGAGTTGAGG CTGGGAGAGG CTCCCTCCTT GGAGTGTTGC
11851 TTTTTTTTGTT TCACCCCTGC CTCTGGAGAT GGGTAGAGGA ACATGAGCTG
11901 ACCTTCTGGG AAGTTAGGTT GGTGAGGAGT TGCTGAGGCA CTGCAGGGCC
11951 ATGCCCAGTA GAGAGGAATG TATAACATTT TAAGAGGCTG AGAGCACCCC
12001 TTGTTGGGCG CATGCCCATG GCAGCTTCCT TCTGCCGATC ATGGGAGAAA
12051 TCAAGCACTT TCACCTAATG GCTAGATGAT TGATTTTGGG ATGAAATTCT
12101 CCACTCCTCT CCTTTACCAC ATCACCACTA TCCTTCCTGC AATACATCCA
12151 CGAGACTCAC TGAGTGGAAA AGGGATAGGA ATGAATGTTC ACCCAGGGCC
12201 AGCTACATGC TAGGCACTGT ACTGGACCAT TTAAATTTGC CACCTCTTAT
12251 GTTCCTCACA TTAATCTTAC AGAGTAGGTA CAGACATACC TATGGATATT
12301 GCAGATTCAG TTCCAGACCA CAGCAATAAA GCAAGTCACA TGAATTTTTT
12351 GCTTTCCTTA GTGCATGTAA AAGTTACATT TCCACTATAT TATAGTTTAT
12401 TAAGTGTGCA ATAGCATTAT GTCTTTAAAA AGCATGTACA TACCTTAATT
12451 TAAAAATACC TTGTTGCTGA AAAATGCTAA CAATCATCTG AGCCTTCAGT
```

FIG.3E

```
12501 GATTGCAGTA GCCTAGGCTA CTATTTTCTA TGTGGGGTTT GCACATTCTG
12551 CCCATGTCTG CGTGGGTTTT CTCTGAGTTC TCCAGCTTCC TCCCACATTC
12601 CAAAGATGTG TATGTTACAT TCATGGGAAT GTCTAAATTG TCGTAATCTT
12651 TTTGCTGGTT GATGGTCTTG CCTTGATGTT GATGCTGCAG GTGGTGGTTG
12701 CTGAAGGTGG GGGAGGCTGT GGCAATTTCT TAAAATAAAA TAAGACAACA
12751 GTGGATTTGC CACATCAATG GACTCTTCCT TTCATGAAAG ATTTCTCTGT
12801 AGCAGATGAT GCTGTTCTAT AGCATTTTAC CCACAGTAGA ATTTCTTTCA
12851 AAACTGGAGG TGGTCCTCTC AAACCCTATG CTACTTTATC GACGAAGTTT
12901 ATGTAGTATT CTAAATCTTT TGTTGTCATT TCAACAGTGT TCATAGCATT
12951 TTCACCCAGA GTAGATTCCA TCTCAAGAAA CCACGATTTT TGCTTATCTG
13001 TAGGAAGCAA ATCCTCATCT GGCCAACTTA TTCATGAGAT TGAAGCAATT
13051 CAGTCATATT TTCAGGCTCC ACTCCTAATT CTAGTTCTCT TGTTATTTCC
13101 ACCACATCTG CAGTTACATC TTCCACTGAA GTCATGAACC CCTCAAAGTC
13151 ATCCATAAGG GTTGGAATCA ACTTCTTCCA AACTGTTAAT GATGTTATTT
13201 TGACCACCTC CCATAAATCA TGAATGTTCC TCATGGCATC TGGAATGGTG
13251 AATTCTTTTT AGAAGTTTTC CAGTTTACTT TGCTGAGGTC CATAAGAGGA
13301 CTCACTGTCT ATGACAACTA TAGCCTTACA AATTGTATTT CTTAAATAAT
13351 TGGACTTGAA AGTCAAAATA CTCCTTGATC CACAGGCTGC AGAAGGGATG
13401 TTGTGTCAGC AGGCATGAAC ACTACTTTAA CCTTGTACAT CTTCATCAGA
13451 GTTCTTGGGT TATCAAGTGT CTTGTAAATA AGCAGTAATA TTTTCAAAGA
13501 AATCTTTTAT TCTGAGCAGT AGGTCTCAAC AGTGGGCTTA AAATATCTAG
13551 TAAACCATGC TGTAAATAGA TGTGCTGGCA CCCAGGCTTC TTTGTTCCAT
13601 TTATAGAGCA CAGGGAGGCT AGATTTAGCA TAATTTTTCA GGGCCCATTC
13651 TTGGAATGGA AATGAGCATT GGCTTCAACT TAAAGTCACC AGCTGCATTA
13701 GCTCCTAACA AGAGAGTCAG CCTGTTCTTT GAAGCTTTGA AGGCAGGCAT
13751 TGACTTCTTC TCTCTAGCTA TGAAAGCCCT AGATGGCATC TTCTTCCCAT
13801 AGAAGGCTGT TTCATCTACA ATGAAAATCT TTTGTTTCAT GTAATCACCT
13851 TCATCAATCA TCTTAGGTGA GTCCTGGA TACCTTGCTG CAGCTTCCCC
13901 ATCAGCTCTC CTTCACCTTG CACTTTTATG ATTATGTTAT GGAGACAACT
13951 TCTTTCTTTC AACCTCTTGA ACCAAACCCT GGCTAGCTTC CTCACTTCCC
14001 CCTCAGCCTT CATGGAATGA AAGAGTTAGG CTCTTCCTCT GGATTAGGCT
14051 TTGGTTTACA GGAATGCTGT GGCTGGTTTG ATCTCCTATT CAGATCATTA
14101 CATTTTCCTG CATGTCAGCA ATAAGGCTGT TTTTNNNNN NNNNNNNNNN
14151 NNNNNNNNNN NNNNNNNNNN NNNNNNNNNN NNNNNNNNNN NNNNNNNNNN
14201 NNNNNNNNNN NNNNNNNNNN NNNNNNNNNN NNNNNNNNNN NNNNNNNNNN
14251 NNNNNNNNNN NNNNNNNNNN NNNNNNNNNN NNNNNNNNNN NNNNNNNNNN
14301 NNNNNNNNNN NNNNNNNNNN NNNNNNNNNN NNNNNNNNNN NNNNNNNNNN
14351 NNNNNNNNNN NNNNNNNNNN NNNNNNNNNN NNNNNNNNNN NNNNNNNNNN
14401 NNNNNNNNNN NNNNNNNNNN NNNNNNNNNN NNNNNNNNNN NNNNNNNNNN
14451 NNNNNNNNNN NNNNNNNNNN NNNNNNNNNN NNNNNNNNNN NNNNNNNNNN
14501 NNNNNNNNNN NNNNNNNNNN NNNNNNNNNN NNNNNNNNNN NNNNNNNNNN
14551 NNNNNNNNNN NNNNNNNNNN NNNNNNNNNN NNNNNNNNNN NNNNNNNNNN
14601 NNNNNNNNNN NNNNNNNNNN NNNNNNNNNN NNNNNNNNNN NNNNNNNNNN
14651 NNNNNNNNNN NNNNNNNNNN NNNNNNNNNN NNNNNNNNNN NNNNNNNNNN
14701 NNNNNNNNNN NNNNNNNNNN NNNNNNNNNN NNNNNNNNNN NNNNNNNNNN
14751 NNN
      (SEQ ID NO: 3)
```

FIG.3F

FEATURES:

| | |
|---|---|
| Exon: | 3251-3464 |
| Intron: | 3465-4655 |
| Exon: | 4656-4719 |
| Intron: | 4720-11561 |
| Exon: | 11562-11592 |

SNPs:

| DNA Position | Major | Minor | Domain | Protein Position | Major | Minor |
|---|---|---|---|---|---|---|
| 3331 | C | T | Exon | 27 | D | D |
| 3389 | C | T | Exon | 47 | P | S |
| 3792 | T | A | Intron | | | |
| 4913 | C | T | Intron | | | |
| 11660 | T | C | Beyond ORF(3') | | | |
| 12008 | G | A | Beyond ORF(3') | | | |

Context:

DNA Position

3331
GGCTGGCTGGTGCTGTGGCCACCTGGGCCTGCATGGGAGTGGATTTTCCTGCAGGTGTCC
TGAGGGAACTGAGGGCTTGAGTAGGGCTGTAATCCAATCTGACTGCAGTTTCCAAAAACT
CCTTTTGCCACCTGTGGAGGGCAGGTTGTGAAGGCCAGACTCCAGATGGCCTGTGAAGAA
ACCCATCTCGACCCATCATTTCTTCTCTCTCCAACAGGGGATGATATTTGAGAAGCTCAG
AATCTGTTCTATGCCCCAATTTTTTCTGTTTCATGCAAGATCTGCCTCCGCTAAAGTATGA
[C,T]
CCCGATGTTGTGGTCACGGATTTTCCGCTTTGGGACAATCCCTGTGAAGCTGTACCAACCC
AAGGCATCCACCTGCACCCTGAAGCCTGGCATCGTGTACTACCACGGTGGCGGGGGCGTC
ATGGGGAGTTTGAGTAAGAACCATTTTCTCAGACCTCCTAAAGGGTGGTGGCACCCCTTA
ACATAACTTGGAAGAATGGGCATCTTCCTGGGACTTAAAGTATGCTATTATTATCAGGGA
ACACCAGGGCAGTTCATGGTTTGCAGATCATTGAGGGGGCAAAAATATGGCATATATTGC

3389
CCTGAGGGAACTGAGGGCTTGAGTAGGGCTGTAATCCAATCTGACTGCAGTTTCCAAAAA
CTCCTTTTGCCACCTGTGGAGGGCAGGTTGTGAAGGCCAGACTCCAGATGGCCTGTGAAG
AAACCCATCTCGACCCATCATTTCTTCTCTCTCCAACAGGGGATGATATTTGAGAAGCTC
AGAATCTGTTCTATGCCCCAATTTTTTCTGTTTCATGCAAGATCTGCCTCCGCTAAAGTAT
GACCCCGATGTTGTGGTCACGGATTTTCCGCTTTGGGACAATCCCTGTGAAGCTGTACCAA
[C,T]
CCAAGGCATCCACCTGCACCCTGAAGCCTGGCATCGTGTACTACCACGGTGGCGGGGGCG
TCATGGGGAGTTTGAGTAAGAACCATTTTCTCAGACCTCCTAAAGGGTGGTGGCACCCCT
TAACATAACTTGGAAGAATGGGCATCTTCCTGGGACTTAAAGTATGCTATTATTATCAGG
GAACACCAGGGCAGTTCATGGTTTGCAGATCATTGAGGGGGCAAAAATATGGCATATATT
GCCCTCTTATGTATCTCCTTATTTACATAAATGTAATCCTTAGTTAAATTAACAATACTG

3792
AAGGGTGGTGGCACCCCTTAACATAACTTGGAAGAATGGGCATCTTCCTGGGACTTAAAG
TATGCTATTATTATCAGGGAACACCAGGGCAGTTCATGGTTTGCAGATCATTGAGGGGGC
AAAAATATGGCATATATTGCCCTCTTATGTATCTCCTTATTTACATAAATGTAATCCTTA
GTTAAATTAACAATACTGTAATATAAGGAAGGATACTGTAAGGTAAAGATCCTGAAATGT

FIG.3G

ACCCTTACTTGCATTTATATGTGTACATATGTATGTACATATAAATGTATACATGTATAT
[T,A]
TCACTATTTTACTTATAATCACCACCTCTATTTAGTTGGAAATAAGGATATTTTAAATGA
AAAGAATTAAAACACAGCATTTTGTTTCACATCAGGTTTTGCTAAGACAAATTCTGGTAC
AGACAGACAGGAAGATTTGAGAAAAATCAATGAGAGGAAAAAGTCACTATTGAGACAATT
TTACTGTCTTAGTTATTACCCCCAGGGAATTAGGGGAGAGGAAACACCTTTATTTGCTTT
CAGTAGTGCTTTCTAATCTGTGGAATGCCAGGGTCCCAGTGTGGGAGCCTTTGAGAATAA

4913    AGGAAGCCTTCCTAGTGAATCTTAAAAACCATTTATTTTCTAGAAACCCACCATGGCATA
TGCTCTCGTTTGTGCAAGGAGAGTGACTCCGTGGTTCTGGCAGTTGGGTGAGTAAAGGGG
AGATCCCAGGGAGCCAGCAAGGAGCAAGGCTCTGATGTGGAGAGATGGGGTGAGAAGTAG
AAATGGGGGTGGGGGGTGGGGGATGGGAGCAGATGGGAGCTGGAGGAAGCCCAGAGGTGG
GGATGGGCTGGGAGAAGCCAGTGAAGAGAGAAAAAGAAGGCGGCTGGGTGTGGTGGCTCA
[C,T]
GCCTGTAATCCCAACACTTTGGGAGGCCACGGTGGGCAGAATGCTTGAGCCCAGGAGTTC
AGACCAGCCTGGGCAACATAGTGAGACCCCATTTTTACAAAAAATACAAAAATTAGCCAG
GTGTGGTGGCATATGTCTGTAGTCCCAGCTACTTGGGAGGCCGAGGAGGAAGAAGCACCT
GAGCCTGGGAGGTTGCAGTGAGCCGTGATTGCGCCACTACACTCAGCCTGGGTGACAGAA
CAAGACCCTGTCTTAAAACAAACAAAACAAAACAAGAAAAAGAGAGTGAAAGAAAAATAA

11660   CAACACTTATTCTACTACAGAAGCTAAATTGAACCCTCAGGCAGGGTACGTGAAAGTGGC
AAGAGATGTCAAGACCACTGGGCAAGTTGGCCAGTTGTTCCTTAGGAATGAAAATTCTTT
TGAAAGGAATGGCCAGGGTCCTCTGCTGGCCCCACTTGGTCTTCTGGAGGCTCTGATCTT
GGTTGGTTAGTGGTCTTTACAGGCCAAGGTCAAGGCCATTGCACAAAAAACCCTGTGCAT
GCCCTTAACTTGCTTTCAGTTGAATATTTGGGCTGAACTATGAGGCAGAGAGGAATCCCA
[T,C]
TGGGTGGCTCCTTGCTGCATTCGCAGTTGACCAGCATGGGGTTTGTTGGAGAAATAGGAA
CCATCCCCTGAAAACACACACTATGGTAGCCACTCAACTGTTGAAAGGCACTGGAGTCCA
ATGGGTGAGGCCGCCTCTGAGACAAGCCTCTGAGTTGAGGCTGGGAGAGGCTCCCTCCTT
GGAGTGTTGCTTTTTTTGTTTCACCCCTGCCTCTGGAGATGGGTAGAGGAACATGAGCTG
ACCTTCTGGGAAGTTAGGTTGGTGAGGAGTTGCTGAGGCACTGCAGGGCCATGCCCAGTA

12008   GGAGAAATAGGAACCATCCCCTGAAAACACACACTATGGTAGCCACTCAACTGTTGAAAG
GCACTGGAGTCCAATGGGTGAGGCCGCCTCTGAGACAAGCCTCTGAGTTGAGGCTGGGAG
AGGCTCCCTCCTTGGAGTGTTGCTTTTTTTGTTTCACCCCTGCCTCTGGAGATGGGTAGA
GGAACATGAGCTGACCTTCTGGGAAGTTAGGTTGGTGAGGAGTTGCTGAGGCACTGCAGG
GCCATGCCCAGTAGAGAGGAATGTATAACATTTTAAGAGGCTGAGAGCACCCCTTGTTGG
[G,A]
CGCATGCCCATGGCAGCTTCCTTCTGCCGATCATGGGAGAAATCAAGCACTTTCACCTAA
TGGCTAGATGATTGATTTTGGGATGAAATTCTCCACTCCTCTCCTTTACCACATCACCAC
TATCCTTCCTGCAATACATCCACGAGACTCACTGAGTGGAAAAGGGATAGGAATGAATGT
TCACCCAGGGCCAGCTACATGCTAGGCACTGTACTGGACCATTTAAATTTGCCACCTCTT
ATGTTCCTCACATTAATCTTACAGAGTAGGTACAGACATACCTATGGATATTGCAGATTC

Chromosome map:
Chromosome 1

FIG.3H

ISOLATED HUMAN LIPASE PROTEINS, NUCLEIC ACID MOLECULES ENCODING HUMAN LIPASE PROTEINS, AND USES THEREOF

FIELD OF THE INVENTION

The present invention is in the field of lipase proteins that are related to the hormone-sensitive lipase(arylacetarnide deacetylase) subfamily, recombinant DNA molecules, and protein production. The present invention specifically provides novel peptides and proteins and nucleic acid molecules encoding such peptide and protein molecules, all of which are useful in the development of human therapeutics and diagnostic compositions and methods.

BACKGROUND OF THE INVENTION

Lipases

The lipases comprise a family of enzymes with the capacity to catalyze hydrolysis of compounds including phospholipids, mono-, di-, and triglycerides, and acyl-coa thioesters. Lipases play important roles in lipid digestion and metabolism. Different lipases are distinguished by their substrate specificity, tissue distribution and subcellular localization.

Lipases have an important role in digestion. Triglycerides make up the predominant type of lipid in the human diet. Prior to absorption in the small intestine, triglycerides are broken down to monoglycerides and free fatty acids to allow solubilization and emulsification before micelle formation in conjunction with bile acids and phospholipids secreted by the liver. Secreted lipases that act within the lumen include lingual, gastric and pancreatic lipases, each having the ability to act under appropriate pH conditions. Modulating the activity of these enzymes has the potential to alter the processing and absorption of dietary fats. This may be important in the treatment of obesity or malabsorption syndromes such as those that occur in the presence of pancreatic insufficiency.

Lipases have an important role in lipid transport and lipoprotein metabolism. Subsequent to absorption across the intestinal mucosa, fatty acids are transported in complexes with cholesterol and protein molecules termed apoliporoteins. These complexes include particles known as chylomicrons, very low density lipoproteins ("VLDLs"), low density lipoproteins ("LDLs") and high density lipoproteins ("HDLs") depending upon their particular forms. Lipoprotein lipase and hepatic lipase are bound to act at the endothelial surfaces of extrahepatic and hepatic tissues, respectively. Deficiencies of these enzymes are associated with pathological levels of circulating lipoprotein particles. Lipoprotein lipase functions as a homodimer and has the dual functions of triglyceride hydrolase and ligand/bridging factor for receptor-mediated lipoprotein uptake. Severe mutations that cause LPL deficiency result in type I hyperlipoproteinemia, while less extreme mutations in LPL are linked to many disorders of lipoprotein metabolism.

Lipases have an important role in lipolysis. Free fatty acids derived from adipose tissue triglycerides are the most important fuel in mammals, providing more than half the caloric needs during fasting. The enzyme hormone-sensitive lipase plays a vital role in the mobilization of free fatty acids from adipose tissue by controlling the rate of lipolysis of stored triglycerides. Hormone sensitive lipase is activated by catecholamines through cyclic AMP-mediated phosphorylation of serine-563. Dephosphorylation is induced by insulin. While mice with homozygous-null mutations of their hormone-sensitive lipase genes induced by homologous recombination have been shown to enlarged adipocytes in their brown adipose tissue and to a lesser extent their white adipose tissue, they are not obese. White adipose tissue from homozygous null mice retain 40% of their wild type triacylglycerol lipase activity suggesting that one or more other, as yet uncharacterized, enzymes also mediate the hydrolysis of triglycerides stored in adipocytes. Hormone-sensitive lipase does not show sequence homology to the other characterized mammalian lipase proteins.

As identified above and in the cited references, lipase proteins are a major target for drug action and development. Accordingly, it is valuable to the field of pharmaceutical development to identify and characterize previously unknown members of the lipase family of proteins. The present invention advances the state of the art by providing previously unidentified human proteins that have homology to known members of the lipase family of proteins.

The present invention has a substantial similarity to microsomal arylacetamide deacetylase (DAC). DAC Full-length cDNA was isolated from a human liver lambda gt 11 library. This clone encodes an open reading frame of 400 amino acids with a deduced molecular mass of 45.7 kDa and contains two putative glycosylation sites. The 3'-untranslated region contains two putative polyadenylation signals competes against the activity of cytosolic arylamine N-acetyltransferase, which catalyzes one of the initial biotransformation pathways for arylamine and heterocyclic amine carcinogens in many species and tissues. Two extended regions of significant sequence homology with hormone-sensitive lipase and with lipase 2 from Moraxella TA144 were identified.

Hormone-sensitive lipase (HSL) is a cytosolic neutral lipase that functions as the rate-limiting enzyme for the mobilization of free fatty acids in adipose tissue. HSL-derived fatty acids are bound by ALBP to facilitate intracellular trafficking of hydrophobic lipids. HSL has broad substrate specificity; in addition to triacylglycerol, HSL can also catalyze the hydrolysis of diacylglycerol, 1 monoacylglycerol, cholesteryl esters, lipoidal esters of steroid hormones, and retinyl esters in adipose tissue. In the rat, HSL is a 767-aa protein that has a molecular mass of 84 kDa on SDS/PAGE. Its primary sequence is unrelated to any of the other known mammalian lipases; however, within its catalytic domain, it shares some sequence similarity with liver arylacetamide deacetylase as well as with esterases isolated from several bacteria. The secondary structure of the C-terminal portion of HSL has been demonstrated to possess homology with some features of the secondary structure of acetylcholinesterase and of fungal lipases from Geotrichum candidum and Candida rugosa, whereas the N-terminal 320 aa have no primary or secondary structural similarity with any known proteins. The activity of HSL against triacylglycerol and cholesteryl ester substrates is regulated acutely via phosphorylation-dephosphorylation reactions. The activation of HSL by fast-acting lipolytic hormones (catecholamines, glucagon, corticotropin) involves a hormone/receptor-induced increase in the cellular concentration of cAMP, which then activates cAMP-dependent protein kinase, resulting in the phosphorylation of HSL and an increase in hydrolytic activity.

Activity determination and immunoblot analysis of DAC in human target tissues for arylamine carcinogens revealed that in extrahepatic tissues, additional enzymes are responsible for any deacetylation activity, whereas a single enzyme predominantly catalyzes this hydrolytic reaction in liver.

The present invention also provide an important tool to study deacetylation and its effects on the metabolic activation of arylamine and heterocyclic amine carcinogens. For a review related to the present invention, see Shen et al., PNAS Vol. 96, Issue 10, 5528–5532, May 11, 1999; Probst et al., J Biol Chem Aug. 26, 1994;269(34):21650–6; Choo et al., (1998). Appl. Environ. Microbiol. 64: 486–491.

Lipase proteins, particularly members of the hormone-sensitive lipase(arylacetamide deacetylase) subfamily, are a major target for drug action and development. Accordingly, it is valuable to the field of pharmaceutical development to identify and characterize previously unknown members of this subfamily of lipase proteins. The present invention advances the state of the art by providing a previously unidentified human lipase proteins that have homology to members of the hormone-sensitive lipase(arylacetamide deacetylase) subfamily.

SUMMARY OF THE INVENTION

The present invention is based in part on the identification of amino acid sequences of human lipase peptides and proteins that are related to the hormone-sensitive lipase (arylacetamide deacetylase) subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate lipase activity in cells and tissues that express the lipase. Experimental data as provided in FIG. 1 indicates expression in the placenta.

DESCRIPTION OF THE FIGURE SHEETS

FIG. 1 provides the nucleotide sequence of a cDNA molecule sequence that encodes the lipase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the placenta.

FIG. 2 provides the predicted amino acid sequence of the lipase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the lipase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, were identified at 6 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a lipase protein or part of a lipase protein and are related to the hormone-sensitive lipase(arylacetamide deacetylase) subfamily. Utilizing these sequences, additional genomic sequences were assembled and transcript and/or cDNA sequences were isolated and characterized. Based on this analysis, the present invention provides amino acid sequences of human lipase peptides and proteins that are related to the hormone-sensitive lipase(arylacetamide deacetylase) subfamily, nucleic acid sequences in the form of transcript sequences, cDNA sequences and/or genomic sequences that encode these lipase peptides and proteins, nucleic acid variation (allelic information), tissue distribution of expression, and information about the closest art known protein/peptide/domain that has structural or sequence homology to the lipase of the present invention.

In addition to being previously unknown, the peptides that are provided in the present invention are selected based on their ability to be used for the development of commercially important products and services. Specifically, the present peptides are selected based on homology and/or structural relatedness to known lipase proteins of the hormone-sensitive lipase(arylacetamide deacetylase) subfamily and the expression pattern observed. Experimental data as provided in FIG. 1 indicates expression in the placenta. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known hormone-sensitive lipase (arylacetamide deacetylase) family or subfamily of lipase proteins.

Specific Embodiments

Peptide Molecules

The present invention provides nucleic acid sequences that encode protein molecules that have been identified as being members of the lipase family of proteins and are related to the hormone-sensitive lipase(arylacetamide deacetylase) subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the lipase peptides of the present invention, lipase peptides, or peptides/proteins of the present invention.

The present invention provides isolated peptide and protein molecules that consist of, consist essentially of, or comprise the amino acid sequences of the lipase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the lipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated lipase peptide can be purified from cells that naturally express it, purified from cells that have been altered to express it (recombinant), or synthesized using known protein synthesis methods. Experimental data as provided in FIG. 1 indicates expression in the placenta. For example, a nucleic acid molecule encoding the lipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the lipase peptides of the present invention are the naturally occurring mature proteins. A brief description of how various types of these proteins can be made/isolated is provided below.

The lipase peptides of the present invention can be attached to heterologous sequences to form chimeric or fusion proteins. Such chimeric and fusion proteins comprise a lipase peptide operatively linked to a heterologous protein having an amino acid sequence not substantially homologous to the lipase peptide. "Operatively linked" indicates that the lipase peptide and the heterologous protein are fused in-frame. The heterologous protein can be fused to the N-terminus or C-terminus of the lipase peptide.

In some uses, the fusion protein does not affect the activity of the lipase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant lipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A lipase peptide-encoding nucleic acid can be cloned into such an expression vector such that the fusion moiety is linked in-frame to the lipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the lipase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the lipase peptides of the present invention as well as being encoded by the same genetic locus as the lipase peptide provided herein. As indicated by the data presented in FIG. 3, the map position was determined to be on chromosome 1 by ePCR.

Allelic variants of a lipase peptide can readily be identified as being a human protein having a high degree (significant) of sequence homology/identity to at least a portion of the lipase peptide as well as being encoded by the same genetic locus as the lipase peptide provided herein. Genetic locus can readily be determined based on the genomic information provided in FIG. 3, such as the genomic sequence mapped to the reference human. As indicated by the data presented in FIG. 3, the map position was determined to be on chromosome 1 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a lipase peptide encoding nucleic acid molecule under stringent conditions as more fully described below.

FIG. 3 provides information on SNPs that have been identified in a gene encoding the lipase protein of the present invention. 6 SNP variants including 1 SNPs in exons were found. SNPs, identified at different nucleotide positions in introns and regions 5' and 3' of the ORF, may affect control/regulatory elements.

Paralogs of a lipase peptide can readily be identified as having some degree of significant sequence homology/identity to at least a portion of the lipase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a lipase peptide encoding nucleic acid molecule under moderate to stringent conditions as more fully described below.

Orthologs of a lipase peptide can readily be identified as having some degree of significant sequence homology/identity to at least a portion of the lipase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a lipase peptide encoding nucleic acid molecule under moderate to stringent conditions, as more fully described below, depending on the degree of relatedness of the two organisms yielding the proteins.

Non-naturally occurring variants of the lipase peptides of the present invention can readily be generated using recombinant techniques. Such variants include, but are not limited to deletions, additions and substitutions in the amino acid sequence of the lipase peptide. For example, one class of substitutions are conserved amino acid substitution. Such substitutions are those that substitute a given amino acid in a lipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant lipase peptides can be fully functional or can lack function in one or more activities, e.g. ability to bind substrate, ability to hydrolyze substrate, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as lipase activity or in assays such as an in vitro proliferative activity. Sites that are critical for binding partner/substrate binding can also be determined by structural analysis such as crystallization, nuclear magnetic resonance or photo affinity labeling (Smith et al., *J. Mol. Biol.* 224:899–904 (1992); de Vos et al. *Science* 255:306–312 (1992)).

The present invention further provides fragments of the lipase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a lipase peptide. Such fragments can be chosen based on the ability to retain one or more of the biological activities of the lipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the lipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in lipase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Post translational Covalent Modification of proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad Sci.* 663:48–62 (1992)).

Accordingly, the lipase peptides of the present invention also encompass derivatives or analogs in which a substituted amino acid residue is not one encoded by the genetic code, in which a substituent group is included, in which the mature lipase peptide is fused with another compound, such as a compound to increase the half-life of the lipase peptide (for example, polyethylene glycol), or in which the additional amino acids are fused to the mature lipase peptide, such as a leader or secretory sequence or a sequence for purification of the mature lipase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a lipase-effector protein interaction or lipase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, lipases isolated from humans and their human/mammalian orthologs serve as targets for identifying agents for use in mammalian therapeutic applications, e.g. a human drug, particularly in modulating a biological or pathological response in a cell or tissue that expresses the lipase. Experimental data as provided in FIG. 1 indicates that lipase proteins of the present invention are expressed in the placenta detected PCR-based tissue screening panel. A large percentage of pharmaceutical agents are being developed that modulate the activity of lipase proteins, particularly members of the hormone-sensitive lipase(arylacetamide deacetylase) subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the placenta. Such uses can readily be determined using the information provided herein, that which is known in the art, and routine experimentation.

The proteins of the present invention (including variants and fragments that may have been disclosed prior to the present invention) are useful for biological assays related to lipases that are related to members of the hormone-sensitive lipase(arylacetamide deacetylase) subfamily. Such assays involve any of the known lipase functions or activities or properties useful for diagnosis and treatment of lipase-related conditions that are specific for the subfamily of lipases that the one of the present invention belongs to, particularly in cells and tissues that express the lipase. Experimental data as provided in FIG. 1 indicates that lipase proteins of the present invention are expressed in the placenta detected PCR-based tissue screening panel.

The proteins of the present invention are also useful in drug screening assays, in cell-based or cell-free systems. Cell-based systems can be native, i.e., cells that normally express the lipase, as a biopsy or expanded in cell culture. Experimental data as provided in FIG. 1 indicates expression in the placenta. In an alternate embodiment, cell-based assays involve recombinant host cells expressing the lipase protein.

The polypeptides can be used to identify compounds that modulate lipase activity of the protein in its natural state or an altered form that causes a specific disease or pathology associated with the lipase. Both the lipases of the present invention and appropriate variants and fragments can be used in high-throughput screens to assay candidate compounds for the ability to bind to the lipase. These compounds can be further screened against a functional lipase to determine the effect of the compound on the lipase activity. Further, these compounds can be tested in animal or invertebrate systems to determine activity/effectiveness. Compounds can be identified that activate (agonist) or inactivate (antagonist) the lipase to a desired degree.

Further, the proteins of the present invention can be used to screen a compound for the ability to stimulate or inhibit interaction between the lipase protein and a molecule that normally interacts with the lipase protein, e.g. a substrate. Such assays typically include the steps of combining the lipase protein with a candidate compound under conditions that allow the lipase protein, or fragment, to interact with the target molecule, and to detect the formation of a complex between the protein and the target or to detect the biochemical consequence of the interaction with the lipase protein and the target, such as any of the associated effects of hydrolysis.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant lipases or appropriate fragments containing mutations that affect lipase function and thus compete for substrate. Accordingly, a fragment that competes for substrate, for example with a higher affinity, or a fragment that binds substrate but does not allow release, is encompassed by the invention.

Any of the biological or biochemical functions mediated by the lipase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the lipase can be assayed. Experimental data as provided in FIG. 1 indicates that lipase proteins of the present invention are expressed in the placenta detected PCR-based tissue screening panel.

Binding and/or activating compounds can also be screened by using chimeric lipase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native lipase. Accordingly, a different set of signal transduction components is available as an end-point assay for activation. This allows for assays to be performed in other than the specific host cell from which the lipase is derived.

The proteins of the present invention are also useful in competition binding assays in methods designed to discover compounds that interact with the lipase (e.g. binding partners and/or ligands). Thus, a compound is exposed to a lipase polypeptide under conditions that allow the compound to bind or to otherwise interact with the polypeptide. Soluble lipase polypeptide is also added to the mixture. If the test compound interacts with the soluble lipase polypeptide, it decreases the amount of complex formed or activity from the lipase target. This type of assay is particularly useful in cases in which compounds are sought that interact with specific regions of the lipase. Thus, the soluble polypeptide that competes with the target lipase region is designed to contain peptide sequences corresponding to the region of interest.

To perform cell free drug screening assays, it is sometimes desirable to immobilize either the lipase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-tansferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of lipase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a lipase-binding protein and a candidate compound are incubated in the lipase protein-presenting wells and the amount of complex trapped in the well can be quantitated. Methods for detecting such complexes, in addition to those described above for the GST-immobilized complexes, include immunodetection of complexes using antibodies reactive with the lipase protein target molecule, or which are reactive with lipase protein and compete with the target molecule, as well as enzyme-linked assays which rely on detecting an enzymatic activity associated with the target molecule.

Agents that modulate one of the lipases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of lipase protein activity identified according to these drug screening assays can be used to treat a subject with a disorder mediated by the lipase pathway, by treating cells or tissues that express the lipase. Experimental data as provided in FIG. 1 indicates expression in the placenta. These methods of treatment include the steps of administering a modulator of lipase activity in a pharmaceutical composition to a subject in need of such treatment, the modulator being identified as described herein.

In yet another aspect of the invention, the lipase proteins can be used as "bait proteins" in a two-hybrid assay or three-hybrid assay (see, e.g., U.S. Pat. No. 5,283,317; Zervos etal. (1993) *Cell* 72:223–232; Madura et al. (1993) *J. Biol. Chem.* 268:12046–12054; Bartel et al. (1993) Biotechniques 14:920–924; Iwabuchi et al. (1993) *Oncogene* 8:1693–1696; and Brent W094/10300), to identify other proteins, which bind to or interact with the lipase and are involved in lipase activity.

The two-hybrid system is based on the modular nature of most transcription factors, which consist of separable DNA-binding and activation domains. Briefly, the assay utilizes two different DNA constructs. In one construct, the gene that codes for a lipase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a lipase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the lipase protein.

This invention further pertains to novel agents identified by the above-described screening assays. Accordingly, it is within the scope of this invention to further use an agent identified as described herein in an appropriate animal model. For example, an agent identified as described herein (e.g., a lipase-modulating agent, an antisense lipase nucleic acid molecule, a lipase-specific antibody, or a lipase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The lipase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the placenta. The method involves contacting a biological sample with a compound capable of interacting with the lipase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered lipase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the lipase protein in which one or more of the lipase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and lipase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the placenta. Accordingly, methods for treatment include the use of the lipase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the lipase proteins. Antibodies can be prepared from any region of the peptide as described herein. However, preferred regions will include those involved in function/activity and/or lipase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that lipase proteins of the present invention are expressed in the placenta detected PCR-based tissue screening panel. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the placenta. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the placenta. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the placenta. Thus, where a specific protein has been correlated with expression in a specific tissue, antibodies that are specific for this protein can be used to identify a tissue type.

The antibodies are also useful for inhibiting protein function, for example, blocking the binding of the lipase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a lipase peptide or protein of the present invention (cDNA, transcript and genomic sequence). Such nucleic acid molecules will consist of, consist essentially of, or comprise a nucleotide sequence that encodes one of the lipase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the lipase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the lipase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 1 by ePCR.

FIG. 3 provides information on SNPs that have been identified in a gene encoding the lipase protein of the present invention. 6 SNP variants including 1 SNPs in exons were found. SNPs, identified at different nucleotide positions in introns and regions 5' and 3' of the ORF, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, were identified at 6 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 1 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that lipase proteins of the present invention are expressed in the placenta detected PCR-based tissue screening panel. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in lipase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a lipase protein, such as by measuring a level of a lipase-encoding nucleic acid in a sample of cells from a subject e.g., mRNA or genomic DNA, or determining if a lipase gene has been mutated. Experimental data as provided in FIG. 1 indicates that lipase proteins of the present invention are expressed in the placenta detected PCR-based tissue screening panel.

Nucleic acid expression assays are useful for drug screening to identify compounds that modulate lipase nucleic acid expression.

The invention thus provides a method for identifying a compound that can be used to treat a disorder associated with nucleic acid expression of the lipase gene, particularly biological and pathological processes that are mediated by the lipase in cells and tissues that express it. Experimental data as provided in FIG. 1 indicates expression in the placenta. The method typically includes assaying the ability of the compound to modulate the expression of the lipase nucleic acid and thus identifying a compound that can be used to treat a disorder characterized by undesired lipase nucleic acid expression. The assays can be performed in cell-based and cell-free systems. Cell-based assays include cells naturally expressing the lipase nucleic acid or recombinant cells genetically engineered to express specific nucleic acid sequences.

The assay for lipase nucleic acid expression can involve direct assay of nucleic acid levels, such as mRNA levels. In this embodiment the regulatory regions of these genes can be operably linked to a reporter gene such as luciferase.

Thus, modulators of lipase gene expression can be identified in a method wherein a cell is contacted with a candidate compound and the expression of mRNA determined. The level of expression of lipase mRNA in the presence of the candidate compound is compared to the level of expression of lipase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate lipase nucleic acid expression in cells and tissues that express the lipase. Experimental data as provided in FIG. 1 indicates that lipase proteins of the present invention are expressed in the placenta detected PCR-based tissue screening panel. Modulation includes both up-regulation (i.e. activation or agonization) or down-regulation (suppression or antagonization) or nucleic acid expression.

Alternatively, a modulator for lipase nucleic acid expression can be a small molecule or drug identified using the screening assays described herein as long as the drug or small molecule inhibits the lipase nucleic acid expression in the cells and tissues that express the protein. Experimental data as provided in FIG. 1 indicates expression in the placenta.

The nucleic acid molecules are also useful for monitoring the effectiveness of modulating compounds on the expression or activity of the lipase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in lipase nucleic acid expression, and particularly in qualitative changes that lead to pathology. The nucleic acid molecules can be used to detect mutations in lipase genes and gene expression products such as mRNA. The nucleic acid molecules can be used as hybridization probes to detect naturally occurring genetic mutations in the lipase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the lipase gene associated with a dysfunction provides a diagnostic tool for an active disease or susceptibility to disease when the disease results from over expression, under expression, or altered expression of a lipase protein.

Individuals carrying mutations in the lipase gene can be detected at the nucleic acid level by a variety of techniques. FIG. 3 provides information on SNPs that have been identified in a gene encoding the lipase protein of the present invention. 6 SNP variants including 1 SNPs in exons were found. SNPs, identified at different nucleotide positions in introns and regions 5' and 3' of the ORF, may affect control/regulatory elements. As indicated by the data presented in FIG. 3, the map position was determined to be on chromosome 1 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a lipase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S I protection or the chemical cleavage method. Furthermore, sequence differences between a mutant lipase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS*

86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the lipase gene in an individual in order to select an appropriate compound or dosage regimen for treatment. FIG. 3 provides information on SNPs that have been identified in a gene encoding the lipase protein of the present invention. 6 SNP variants including 1 SNPs in exons were found. SNPs, identified at different nucleotide positions in introns and regions 5' and 3' of the ORF, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control lipase gene expression in cells, tissues, and organisms. A DNA antisense nucleic acid molecule is designed to be complementary to a region of the gene involved in transcription, preventing transcription and hence production of lipase protein. An antisense RNA or DNA nucleic acid molecule would hybridize to the mRNA and thus block translation of mRNA into lipase protein.

Alternatively, a class of antisense molecules can be used to inactivate mRNA in order to decrease expression of lipase nucleic acid. Accordingly, these molecules can treat a disorder characterized by abnormal or undesired lipase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the lipase protein, such as substrate binding.

The nucleic acid molecules also provide vectors for gene therapy in patients containing cells that are aberrant in lipase gene expression. Thus, recombinant cells, which include the patient's cells that have been engineered ex vivo and returned to the patient, are introduced into an individual where the cells produce the desired lipase protein to treat the individual.

The invention also encompasses kits for detecting the presence of a lipase nucleic acid in a biological sample. Experimental data as provided in FIG. 1 indicates that lipase proteins of the present invention are expressed in the placenta detected PCR-based tissue screening panel. For example, the kit can comprise reagents such as a labeled or labelable nucleic acid or agent capable of detecting lipase nucleic acid in a biological sample; means for determining the amount of lipase nucleic acid in the sample; and means for comparing the amount of lipase nucleic acid in the sample with a standard. The compound or agent can be packaged in a suitable container. The kit can further comprise instructions for using the kit to detect lipase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot)

blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the lipase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the lipase gene of the present invention. FIG. 3 provides information on SNPs that have been identified in a gene encoding the lipase protein of the present invention. 6 SNP variants including 1 SNPs in exons were found. SNPs, identified at different nucleotide positions in introns and regions 5' and 3' of the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fl. Vol. 1 (1982), Vol. 2 (1983), Vol. 3 (1985); Tijssen, P., Practice and Theory of Enzyme Immunoassays: *Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified lipase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterolipase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11 d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufinan et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning. A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as lipases, appropriate secretion signals are incorporated into the vector. The signal sequence can be endogenous to the peptides or heterologous to these peptides.

Where the peptide is not secreted into the medium, which is typically the case with lipases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a lipase protein or peptide that can be further purified to produce desired amounts of lipase protein or fragments. Thus, host cells containing expression vectors are useful for peptide production.

Host cells are also useful for conducting cell-based assays involving the lipase protein or lipase protein fragments, such as those described above as well as other formats known in the art. Thus, a recombinant host cell expressing a native lipase protein is useful for assaying compounds that stimulate or inhibit lipase protein function.

Host cells are also useful for identifying lipase protein mutants in which these functions are affected. If the mutants naturally occur and give rise to a pathology, host cells containing the mutations are useful to assay compounds that have a desired effect on the mutant lipase protein (for example, stimulating or inhibiting function) which may not be indicated by their effect on the native lipase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a lipase protein and identifying and evaluating modulators of lipase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the lipase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the lipase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, and lipase protein activation, may not be evident from in vitro cell-free or cell-based assays. Accordingly, it is useful to provide non-human transgenic animals to assay in vivo lipase protein function, including substrate interaction, the effect of specific mutant lipase proteins on lipase protein function and substrate interaction, and the effect of chimeric lipase proteins. It is also possible to assess the effect of null mutations, that is mutations that substantially or completely eliminate one or more lipase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule encoding an arylacetamide deacetylase consisting of a nucleotide sequence selected from the group consisting of:

(a) a nucleotide sequence that encodes a protein comprising the amino acid sequence of SEQ ID NO:2;

(b) a nucleic acid molecule consisting of the nucleic acid sequence of SEQ ID NO:1; and (c) a nucleic acid molecule consisting of the nucleic acid sequence of SEQ ID NO:3.

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of claim 4.

* * * * *

SEQUENCE LISTING

<160> NUMBER OF SEQ ID NOS: 5

<210> SEQ ID NO 1
<211> LENGTH: 4396
<212> TYPE: DNA
<213> ORGANISM: Human

<400> SEQUENCE: 1

```
gattttagtc ccagacagcc gagccagatc cggggcgaac gcaaagaaca gagggagaag        60
gggagcaggg aggcgagagg agggcagtac atgtaagcca ggtcaacaga ggcacatcac       120
ggactaaaga agcgggacag gcggggggaag aagaagaaaa agaaagggta accctaaaac       180
gagaagcggc gggaggcgac aagcttaaga ccggtacagg acgagaaaac ccaagcaata       240
atacccccca gcaaaaagga gtatagttcc agcgaaagag cgaaacggat atctacacgc       300
cggcgaacac gaccacggga cgcagagagc aaggcaaaag aaaaaaaagg tgtaaagaag       360
caggggagcg gacctgggaa gggcgacaga gagggggaag caaccataga cggcctggac       420
```

-continued

| | |
|---|---|
| ataaatgagc ctggcaacag cagcgcgcgt tcgcagtaga agaccctcta tgggtcgcgg | 480 |
| gcaggcaagg ggtcgctgtg cacatccctg cagcggttgg ccaccctgtg aaactgagag | 540 |
| tcctccattg catcttccag ctgctgttga cttgggggat gatatttgag aagctcagaa | 600 |
| tctgttctat gccccaattt ttctgtttca tgcaagatct gcctccgcta agtatgacc | 660 |
| ccgatgttgt ggtcacggat ttctgctttg ggacaatccc tgtgaagctg taccaaccca | 720 |
| aggcatccac ctgcaccctg aagcctggca tcgtgtacta ccacggtggc gggggcgtca | 780 |
| tggggagttt gaaaacccac catggcatat gctctcgttt gtgcaaggag agtgactccg | 840 |
| tggttctggc agttggttac cgcaagttac ctaagcataa gtttccagtg ccagtaagag | 900 |
| actgcttggt ggccaccatc cacttcctga agtccctgga tgcatatgga gtggatccag | 960 |
| cccgggttgt ggtctgcggt gacagtttcg gaggggcaat agccgcagtg gtttgtcaac | 1020 |
| aacttgtgga caggccagat ctgccccgga tccgggctca gatcctgatc tatgccattc | 1080 |
| tccaagccct ggatttacaa accccttcgt ttcaacagag gaaaaacatc ccactgctca | 1140 |
| cctggagttt catctgctac tttttttttc aaaacctgga tttcagctcc tcctggcaag | 1200 |
| aggtcatcat gaaaggtgcc catttgcctg ctgaagtctg ggaaaagtac agaaagtggt | 1260 |
| tgggcccaga aaacatccct gagaggttta aggagagggg ttaccaactg aagcccatg | 1320 |
| agcccatgaa tgaagctgct tacttggaag taagtgttgt cctggatgtg atgtgctcgc | 1380 |
| ccctgattgc agaagatgac atagtgtctc agctcccgga aacctgcatc gtgagctgtg | 1440 |
| agtatgatgc tctccgggac aattcactgt tgtacaagaa aaggctggaa gacctgggag | 1500 |
| tgcccgtgac ctggcaccat atggaggatg gtttccatgg agtgctcagg accattgaca | 1560 |
| tgagcttctt gcactttccc tgctccatga gaattctgag tgcattagtt caatttgtaa | 1620 |
| agggactgtg accatctttc ttctctgctg gtactgcggt gtggattcca ctggcatcca | 1680 |
| gcctcccaca gggctctctg ttgctgattt aggtggtgca tagtggggct agggaggggg | 1740 |
| tagaggttgc tgtcaccttt ctggtccagg ttctagaacc acacaatgca tgctcctgat | 1800 |
| gtccagagga cgtggtagaa aagacaggtt tggaggtggg agtgtggctg tctctattct | 1860 |
| ctgttgggaa aacctgggct gacaatattc agtggccatt tgtgggagtg aatcagccgg | 1920 |
| taagagctgt tctcagcctc cctaagggc agttcaggct cccagattga tccagactgt | 1980 |
| gtgtgacttt cgtccatttg acttgacttt ggaatagcac aagggcatca tgtacttcac | 2040 |
| gaggcttttcc caatgtggct cagaggcagg agctctgatg ctctgggctg ctgtgaggtg | 2100 |
| gtggtggtgg tagagaaact ggcttcaccc acctactctt ctgtgaacag tagtgacttt | 2160 |
| tcccgctgtt tctcagcctc tgggatcaga gtcttcactg tctgggctgg aaactttaag | 2220 |
| atagaatgga tagagcttcc acagtggttg gcatctagtg gtggatgaag acagcctgca | 2280 |
| gctgcccgac ttgggggagct ctggagctcc tggaatcaaa gcctgtcttc caaccagaag | 2340 |
| ccccaaggca atgttctaag aatttgagaa agagaagttgg gagggaagtg gggtcctgag | 2400 |
| ttagagaccc atgaaggctg agtctaacca gataaccctg tccacagtgc aaagtcaaga | 2460 |
| cagccaaagg aacagaagat gtatttgtga aaactatttc tttttttaaga catggaacca | 2520 |
| actcaaattg gcctctatta gaaagacaat agattggctt aggtagggt gcatgctagg | 2580 |
| catacatcag gcaaggtttg atccaggaac tcacacagtg ccatcagctg tcctgtcttc | 2640 |
| tctgctctgc tcttctctcc tctgtgttaa tgccaccttc tcctcttcat acggtggcac | 2700 |
| tgagcagctt catgcctacc ttcctccagg gtcaagttca ttatcatgga cttgcctcat | 2760 |
| gctcagcagt cccagaaaaa agcctaattg caacttgatg gctttgttgg ctttctgagc | 2820 |

-continued

```
aatgtgtcca gttgccacag tgaagggaat ggaataatct aactcaccat tcccaagtcc    2880
tatgccatcc tgagagtggg gggtggagtc aattcacctt ggtgcttgga ctaagcatga    2940
ggtggtgagt gacaacgttc ctaattgaag ggtagggtaa atggttgttg ggtggacacc    3000
aacacttatt ctactacaga agctaaattg aaccctcagg cagggtacgt gaaagtggca    3060
agagatgtca agaccactgg gcaagttggc cagttgttcc ttaggaatga aaattctttt    3120
gaaaggaatg gccagggtcc tctgctggcc ccacttggtc ttctggaggc tctgatcttg    3180
gttggttagt ggtctttaca ggccaaggtc aaggccattg cacaaaaaac cctgtgcatg    3240
cccttaactt gctttcagtt gaatatttgg gctgaactat gaggcagaga ggaatcccat    3300
tgggtggctc cttgctgcat tcgcagttga ccagcatggg gtttgttgga gaataggaa     3360
ccatcccctg aaaacacaca ctatggtagc cactcaactg ttgaaaggca ctggagtcca    3420
atgggtgagg ccgcctctga gacaagcctc tgagttgagg ctgggagagg ctccctcctt    3480
ggagtgttgc tttttttgtt tcaccctgc ctctggagat gggtagagga acatgagctg     3540
accttctggg aagttaggtt ggtgaggagt tgctgaggca ctgcagggcc atgcccagta    3600
gagaggaatg tataacattt taagaggctg agagcacccc ttgttgggcg catgcccatg    3660
gcagcttcct tctgccgatc atgggagaaa tcaagcactt tcacctaatg gctagatgat    3720
tgattttggg atgaaattct ccactcctct cctttaccac atcaccacta tccttcctgc    3780
aatacatcca cgagactcac tgagtggaaa agggatagga atgaatgttc acccagggcc    3840
agctacatgc taggcactgt actggaccat ttaaatttgc cacctcttat gttcctcaca    3900
ttaatcttac agagtaggta cagacatacc tatggatatt gcagattcag ttccagacca    3960
cagcaataaa gcaagtcaca tgaatttttt gctttcctta gtgcatgtaa aagttacatt    4020
tccactatat tatagtttat taagtgtgca atagcattat gtctttaaaa agcatgtaca    4080
taccttaatt taaaaatacc ttgttgctga aaaatgctaa caatcatctg agccttcagt    4140
gattgcagta gcctaggcta ctattttcta tgtggggttt gcacattctg cccatgtctg    4200
cgtgggtttt ctctgagttc tccagcttcc tcccacattc caaagatgtg tatgttacat    4260
tcatgggaat gtctaaattg tcgtaatctt tttgctggtt gatggtcttg ccttgatgtt    4320
gatgctgcag gtggtggttg ctgaaggtgg gggaggctgt ggcaatttct taaaataaaa    4380
taagacaaca gtgaaa                                                   4396
```

<210> SEQ ID NO 2
<211> LENGTH: 350
<212> TYPE: PRT
<213> ORGANISM: Human

<400> SEQUENCE: 2

```
Met Ile Phe Glu Lys Leu Arg Ile Cys Ser Met Pro Gln Phe Phe Cys
 1               5                  10                  15

Phe Met Gln Asp Leu Pro Pro Leu Lys Tyr Asp Pro Asp Val Val Val
            20                  25                  30

Thr Asp Phe Cys Phe Gly Thr Ile Pro Val Lys Leu Tyr Gln Pro Lys
        35                  40                  45

Ala Ser Thr Cys Thr Leu Lys Pro Gly Ile Val Tyr Tyr His Gly Gly
    50                  55                  60

Gly Gly Val Met Gly Ser Leu Thr His His Gly Ile Cys Ser Arg
65                  70                  75                  80

Leu Cys Lys Glu Ser Asp Ser Val Val Leu Ala Val Gly Tyr Arg Lys
```

-continued

```
                    85                  90                  95
Leu Pro Lys His Lys Phe Pro Val Pro Val Arg Asp Cys Leu Val Ala
                100                 105                 110
Thr Ile His Phe Leu Lys Ser Leu Asp Ala Tyr Gly Val Asp Pro Ala
            115                 120                 125
Arg Val Val Cys Gly Asp Ser Phe Gly Gly Ala Ile Ala Ala Val
        130                 135                 140
Val Cys Gln Gln Leu Val Asp Arg Pro Asp Leu Pro Arg Ile Arg Ala
145                 150                 155                 160
Gln Ile Leu Ile Tyr Ala Ile Leu Gln Ala Leu Asp Leu Gln Thr Pro
                165                 170                 175
Ser Phe Gln Gln Arg Lys Asn Ile Pro Leu Leu Thr Trp Ser Phe Ile
            180                 185                 190
Cys Tyr Phe Phe Phe Gln Asn Leu Asp Phe Ser Ser Ser Trp Gln Glu
        195                 200                 205
Val Ile Met Lys Gly Ala His Leu Pro Ala Glu Val Trp Glu Lys Tyr
    210                 215                 220
Arg Lys Trp Leu Gly Pro Glu Asn Ile Pro Glu Arg Phe Lys Glu Arg
225                 230                 235                 240
Gly Tyr Gln Leu Lys Pro His Glu Pro Met Asn Glu Ala Ala Tyr Leu
                245                 250                 255
Glu Val Ser Val Val Leu Asp Val Met Cys Ser Pro Leu Ile Ala Glu
            260                 265                 270
Asp Asp Ile Val Ser Gln Leu Pro Glu Thr Cys Ile Val Ser Cys Glu
        275                 280                 285
Tyr Asp Ala Leu Arg Asp Asn Ser Leu Leu Tyr Lys Lys Arg Leu Glu
    290                 295                 300
Asp Leu Gly Val Pro Val Thr Trp His His Met Glu Asp Gly Phe His
305                 310                 315                 320
Gly Val Leu Arg Thr Ile Asp Met Ser Phe Leu His Phe Pro Cys Ser
                325                 330                 335
Met Arg Ile Leu Ser Ala Leu Val Gln Phe Val Lys Gly Leu
            340                 345                 350
```

<210> SEQ ID NO 3
<211> LENGTH: 14753
<212> TYPE: DNA
<213> ORGANISM: Human
<220> FEATURE:
<221> NAME/KEY: misc_feature
<222> LOCATION: (1)...(14753)
<223> OTHER INFORMATION: n = A,T,C or G

<400> SEQUENCE: 3

```
gggtcactct gtgggtcatt tgcagccttt tttcactgtg cacatccctg cagcggttgg      60
ccaccctgtg aaactgagaa gtcctccatt gcatcttcca gctgctgttg acttgggtga     120
gttttgtgct ttatgtgtcc cctccagctg accattaagg aaggcggcag gaaaaatcac     180
acaccggaag cttctagctg aatgaacacc ggtatcatgg ggcctgcagt gacagctgat     240
cagaccttct gaaatgtgca taatccctat taggtggttc tcagcctctt tgggtgtttc     300
tgaagctggc cctggctaat attcacaaaa ttcaaagaat gatctgcttt ctcagttaac     360
agaaagaaaa aaccagtctg gttctattca cctgagtgtc tcccgctgac ttcttttttg     420
ttgttgttgg tttgttttat ttttaaaatt gaggtaaaat atgcatataa aatttaccat     480
ctttcgcatt tttaagtgta cctttcacgt gtccataaat gtgtccatat tattcacagc     540
```

-continued

```
actcaccact ctcagaagtt gtgaagatat gaatgaattt tcctgagtct ctgggccccc      600
actgctatct acctgttagc tagagccagc aagccacaaa gtaaaagggt agcggatgag      660
tagattagtg ccggtgagca aaattacaga atgtgacttt aaaaatatgt tgttgctttt      720
gagagctaga aagctgccta gggaatatag tttggttctg cttctggtgt aatttgttaa      780
aatacctgta aatggaactg tgtaggtgtt gcccaatacg gatttcttgt acttttctt       840
gtgccttgac agaaactgaa tatacaaaat attttttgta agtttcttac ataacgaaaa      900
gcaattgcca gtgcctcttc tcaagagaca ccctaggtgt gtcttctatg ctattcaaaa      960
taatttctat gctattcaaa gaatgtagc tattacctaa agagaagat cccgggaact       1020
ctaggcttct gatctccagt cagctttat aagatgcagt gattgggtcc taggttttcc      1080
taccettgat gctcagattc tgtagtccag gctcccaaat acagtgactc aatttcctct     1140
tttgcaaagt agggaaaatt gctcctactt cacaggggtt tgtggagact ccatgaataa     1200
ccctctccag aaggcttatt ataatgcctg acacagaggg agccctcctt aaatagtagc     1260
cattgttact cttttgttgat tcttttattt tttatgcaaa gatgtgttat gcaactgctg    1320
tgtgtcctac gccagtcctg ggctctaggg ccaatgacag gtgagagagg taaagttcca    1380
caggtctgcc tttagggagc ttgtagggtc caggcagtgg gcagcgggga agtggtctat    1440
aaagaagcta acccacaata gaacaagcta cagataaaca gcttcccaaa gcggagaatg    1500
caaggaggac agcaaaaccc gtcagggga ccgagcaggg cttctctcct ggggcatctt     1560
gagccccgg ggccacagaa cacaaggggg tcatggattt ggatcacaga acataagggg    1620
gtcatggatt tgggtcacag aacacaaggg ggtcatggat ttggatgggg tcaaaattac    1680
cccatgttca caactaactt ccaattgaaa ttcttctcat gaggaatgaa ggcaacaaac    1740
cacagtcctg aaagccagac ctcgactttt caccaagaga aatcagacat atttgcattg    1800
cctattagat attgcgaaaa ctcatgtatt ctcctcattt ctttgaaact agggtagtat    1860
caggcagcag ttagatctta ttactctatg tgctagtaag gaagaaccta tattattatg    1920
acatacattt taatattttg ataagtatat ttaaataaca ctgcttttct ttataatccc    1980
atgtatttat tttatgtatt taaaaatgtt ctgggctggg tgtagtggct tacacctgta    2040
atcccagcac tttgggaggc tgaggtggga ggactgtttg agtccaggag tttgagacca    2100
gcctgggtga cataatgagg cctcttctct cctaaaaaaa aaaaaaaaa aaaaagttct     2160
caaatgaggc ctgcagcttt tcccaaggcc aaaatggctg tggcacagac aaggattagg    2220
aaacactgga aaggataccc agagggagag ccctctttat ttacgtattt ttaactcttt    2280
tttttttgagc tggagtttta ctcttgttgc ccaggctgga gtgcaatggc atgatctcgg   2340
cttactgcaa cctctgcctc tagggttcaa gagattcttc tgcctcagcc tctcgagtag    2400
ccgggaatac aggagcccac caccacaccc acccggctaa ttttttgtatt ttcagtagag    2460
actgggtttc accatgttgg ccaggctggc cttgaactcc tgacctcaag tgacccacca    2520
gccttggcct cccaaagtgc tgggattaca ggtatcagcc actgtgcctg gctgtatttt    2580
caaccctta tgcaaacttt gacatatacc aaaggggaac agggtgccca ctctccagtg     2640
tcaccatcac tgactcctgg cctgtctccc ttccctgtgt ccctaaatgt ctctaacttt    2700
tccctcattt tcatttattt aagaagccaa tggacatcat attattttat cctaaaaatt    2760
ttcagtaggc attttcaaaa gatatgaact cccccttcct gttttaaaa aatgtaccca    2820
cactatagtt agctacacag gcttggggtg gccagattgg ctgggacggc acaggaaggc    2880
```

-continued

| | |
|---|---|
| ctccctggaa acagatgttg cgcccaggct gaggtggagc agggcctcgt ggtggaggtg | 2940 |
| ggtgttgcaa gtagagggac catcaagggt gcccagaagc ctggcttgta gtggctgcag | 3000 |
| tggaaggtgt caggagagtg ggttgagagg ggctggctgg tgctgtggcc acctgggcct | 3060 |
| gcatgggagt ggattttcct gcaggtgtcc tgagggaact gagggcttga gtagggctgt | 3120 |
| aatccaatct gactgcagtt tccaaaaact ccttttgcca cctgtggagg gcaggttgtg | 3180 |
| aaggccagac tccagatggc ctgtgaagaa acccatctcg acccatcatt tcttctctct | 3240 |
| ccaacagggg atgatatttg agaagctcag aatctgttct atgccccaat ttttctgttt | 3300 |
| catgcaagat ctgcctccgc taaagtatga ccccgatgtt gtggtcacgg atttccgctt | 3360 |
| tgggacaatc cctgtgaagc tgtaccaacc caaggcatcc acctgcaccc tgaagcctgg | 3420 |
| catcgtgtac taccacggtg gcgggggcgt catggggagt ttgagtaaga accatttttct | 3480 |
| cagacctcct aaagggtggt ggcaccccctt aacataactt ggaagaatgg gcatcttcct | 3540 |
| gggacttaaa gtatgctatt attatcaggg aacaccaggg cagttcatgg tttgcagatc | 3600 |
| attgaggggg caaaaatatg gcatatattg ccctcttatg tatctcctta tttacataaa | 3660 |
| tgtaatcctt agttaaatta acaatactgt aatataagga aggatactgt aagtaaaga | 3720 |
| tcctgaaatg tacccttact tgcatttata tgtgtacata tgtatgtaca tataaatgta | 3780 |
| tacatgtata tttcactatt ttacttataa tcaccacctc tatttagttg gaaataagga | 3840 |
| tattttaaat gaaagaatt aaaacacagc attttgtttc acatcaggtt ttgctaagac | 3900 |
| aaattctggt acagacagac aggaagattt gagaaaaatc aatgagagga aaagtcact | 3960 |
| attgagacaa ttttactgtc ttagttatta cccccaggga attaggggag aggaaacacc | 4020 |
| tttatttgct ttcagtagtg ctttctaatc tgtggaatgc cagggtccca gtgtgggagc | 4080 |
| ctttgagaat aaaggattta atgcaatggt ggtgtggttt ggtctgtatg agaatgatag | 4140 |
| taacagccaa tatttattaa gcaatattca ttaatattac taattacatg caggcactgt | 4200 |
| gagaaccctcta tatgtggatg atctcattcc aactccaaca ctctacgagt tagatatttt | 4260 |
| cattacccca gttcacagat gaggaaatca agcctcagga ggttaagaga cttgctaggc | 4320 |
| actatgttag ctcaagctag aaaggggcaa agttgagatt tgaactccag tctgaatcca | 4380 |
| gagctcacac cctaaacctc tgcgttctac agtcaaagag cttcacagat atttttaatg | 4440 |
| gcttgtagga tggattggag ggtgggcgtc ttagagaaag ttgttcaggc agtaccacga | 4500 |
| aggagaatca gtgagaagat tgaccggaag tttgctggag tagaggaaaa cctagtcggc | 4560 |
| atcggcccaa gtgctgtgtc tgtaggaaga agacggtgac aatggctggc aaaggaagcc | 4620 |
| ttcctagtga atcttaaaaa ccatttattt tctagaaacc caccatggca tatgctctcg | 4680 |
| tttgtgcaag gagagtgact ccgtggttct ggcagttggg tgagtaaagg ggagatccca | 4740 |
| gggagccagc aaggagcaag gctctgatgt ggagagatgg ggtgagaagt agaaatgggg | 4800 |
| gtgggggtg ggggatggga gcagatggga gctggaggaa gcccagaggt ggggatgggc | 4860 |
| tgggagaagc cagtgaagag agaaaaagaa ggcggctggg tgtggtggct cacgcctgta | 4920 |
| atcccaacac tttgggaggc cacggtgggc agaatgcttg agcccaggag ttcagaccag | 4980 |
| cctgggcaac atagtgagac ccattttta caaaaatac aaaaattagc caggtgtggt | 5040 |
| ggcatatgtc tgtagtccca gctacttggg aggccgagga ggaagaagca cctgagcctg | 5100 |
| ggaggttgca gtgagccgtg attgcgccac tacactcagc ctgggtgaca gaacaagacc | 5160 |
| ctgtcttaaa acaaacaaaa caaaacaaga aaaagagagt gaaagaaaaa taaggggagg | 5220 |
| tgaagagaga tggagagaca gagaatgggg aacccccttcc tctgtgcatg tgggccttgg | 5280 |

```
gtttgtttaa acagaggcgt tttgtgcatt ttgaagctgg gtaggaggtg gtcttttta      5340
agcagttcag gtgcagagtt tcactgcagg aacacttgga caacatagct cttctttgag     5400
taaaacaacc ctgcacctcc ttctgctaaa tgcctgtggt accccgcacc atcactcaaa     5460
caacccgaaa tgctgccacg ttcacttcca agtgctccca aaagggaggt cccctggct      5520
gagacccact gaagaaagtg agaaaaacaa aaacaaaaac aaacccattg tctctcctaa     5580
cagatctctg acagtcaccg cccagcctgg agcctcaaag agggcgtgnn nnnnnnnnn      5640
nnnnnnnnnn nnnnnnnnnn nnnnnnnnnn nnnnnnnnnn nnnnnnnnnn nnnnnnnnnn     5700
nnnnnnnnnn nnnnnnnnnn nnnnnnnnnn nnnnnnnnnn nnnnnnnnnn nnnnnnnnnn     5760
nnnnnnnnnn nnnnnnnnnn nnnnnnnnnn nnnnnnnnnn nnnnnnnnnn nnnnnnnnnn     5820
nnnnnnnnnn nnnnnnnnnn nnnnnnnnnn nnnnnnnnnn nnnnnnnnnn nnnnnnnnnn     5880
nnnnnnnnnn nnnnnnnnnn nnnnnnnnnn nnnnnnnnnn nnnnnnnnnn nnnnnnnnnn     5940
nnnnnnnnnn nnnnnnnnnn nnnnnnnnnn nnnnnnnnnn nnnnnnnnnn nnnnnnnnnn     6000
nnnnnnnnnn nnnnnnnnnn nnnnnnnnnn nnnnnnnnnn nnnnnnnnnn nnnnnnnnnn     6060
nnnnnnnnnn nnnnnnnnnn nnnnnnnnnn nnnnnnnnnn nnnnnnnnnn nnnnnnnnnn     6120
nnnnnnnnnn nnnnnnnnnn nnnnnnnnnn nnnnnnnnnn nnnnnnnnnn nnnnnnnnnn     6180
nnnnnnnnnn nnnnnnnnnn nnnnnnnnnn nnnnnnnnnn nnnnnnnnnn nnnnnnnnnn     6240
nnnnnnnnnn nnnnnnnnnn nnnnnnnnnn nnnnnnnnnn nnnnnnnnnn nnnnnnnnnn     6300
nnnnnnnnnn nnnnnnnnnn nnnnnnnnnn nnnnnnnnnn nnnnnnnnnn nnnnnnnnnn     6360
nnnnnnnnnn nnnnnnnnnn nnnnnnnnnn nnnnnnnnnn nnnnnnnnnn nnnnnnnnnn     6420
nnnnnnnnnn nnnnnnnnnn nnnnnnnnnn nnnnnnnnnn nnnnnnnnnn nnnnnnnnnn     6480
nnnnnnnnnn nnnnnnnnnn nnnnnnnnnn nnnnnnnnnn nnnnnnnnnn nnnnnnnnnn     6540
nnnnnnnnnn nnnnnnnnnn nnnnnnnnnn nnnnnnnnnn nnnnnnnnnn nnnnnnnnnn     6600
nnnnnnnnnn nnnnnnnnnn nnnnnnnnnn nnnnnnnnnn nnnnnnnnnn nnnnnnnnnn     6660
nnnnnnnnnn nnnnnnnnnn nnnnnnnnnn nnnnnnnnnn nnnnnnnnnn nnnnnnnnnn     6720
nnnnnnnnnn nnnnnnnnnn nnnnnnnnnn nnnnnnnnnn nnnnnnnnnn nnnnnnnnnn     6780
nnnnnnnnnn nnnnnnnnnn nnnnnnnnnn nnnnnnnnnn nnnnnnnnnn nnnnnnnnnn     6840
nnnnnnnnnn nnnnnnnnnn nnnnnnnnnn nnnnnnnnnn nnnnnnnnnn nnnnnnnnnn     6900
nnnnnnnnnn nnnnnnnnnn nnnnnnnnnn nnnnnnnnnn nnnnnnnnnn nnnnnnnnnn     6960
nnnnnnnnnn nnnnnnnnnn nnnnnnnnnn nnnnnnnnnn nnnnnnnnnn nnnnnnnnnn     7020
nnnnnnnnnn nnnnnnnnnn nnnnnnnnnn nnnnnnnnnn nnnnnnnnnn nnnnnnnnnn     7080
nnnnnnnnnn nnnnnnnnnn nnnnnnnnnn nnnnnnnnnn nnnnnnnnnn nnnnnnnnnn     7140
nnnnnnnnnn nnnnnnnnnn nnnnnnnnnn nnnnnnnnnn nnnnnnnnnn nnnnnnnnnn     7200
nnnnnnnnnn nnnnnnnnnn nnnnnnnnnn nnnnnnnnnn nnnnnnnnnn nnnnnnnnnn     7260
nnnnnnnnnn nnnnnnnnnn nnnnnnnnnn nnnnnnnnnn nnnnnnnnnn nnnnnnnnnn     7320
nnnnnnnnnn nnnnnnnnnn nnnnnnnnnn nnnnnnnnnn nnnnnnnnnn nnnnnnnnnn     7380
nnnnnnnnnn nnnnnnnnnn nnnnnnnnnn nnnnnnnnnn nnnnnnnnnn nnnnnnnnnn     7440
nnnnnnnnnn nnnnnnnnnn nnnnnnnnnn nnnnnnnnnn nnnnnnnnnn nnnnnnnnnn     7500
nnnnnnnnnn nnnnnnnnnn nnnnnnnnnn nnnnnnnnnn nnnnnnnnnn nnnnnnnnnn     7560
nnnnnnnnnn nnnnnnnnnn nnnnnnnnnn nnnnnnnnnn nnnnnnnnnn nnnnnnnnnn     7620
```

```
nnnnnnnnnn nnnnnnnnnn nnnnnnnnnn nnnnnnnnnn nnnnnnnnnn nnnnnnnnnn      7680
nnnnnnnnnn nnnnnnnnnn nnnnnnnnnn nnnnnnnnnn nnnnnnnnnn nnnnnnnnnn      7740
nnnnnnnnnn nnnnnnnnnn nnnnnnnnnn nnnnnnnnnn nnnnnnnnnn nnnnnnnnnn      7800
nnnnnnnnnn nnnnnnnnnn nnnnnnnnnn nnnnnnnnnn nnnnnnnnnn nnnnnnnnnn      7860
nnnnnnnnnn nnnnnnnnnn nnnnnnnnnn nnnnnnnnnn nnnnnnnnnn nnnnnnnnnn      7920
nnnnnnnnnn nnnnnnnnnn nnnnnnnnnn nnnnnnnnnn nnnnnnnnnn nnnnnnnnnn      7980
nnnnnnnnnn nnnnnnnnnn nnnnnnnnnn nnnnnnnnnn nnnnnnnnnn nnnnnnnnnn      8040
nnnnnnnnnn nnnnnnnnnn nnnnnnnnnn nnnnnnnnnn nnnnnnnnnn nnnnnnnnnn      8100
nnnnnnnnnn nnnnnnnnnn nnnnnnnnnn nnnnnnnnnn nnnnnnnnnn nnnnnnnnnn      8160
nnnnnnnnnn nnnnnnnnnn nnnnnnnnnn nnnnnnnnnn nnnnnnnnnn nnnnnnnnnn      8220
nnnnnnnnnn nnnnnnnnnn nnnnnnnnnn nnnnnnnnnn nnnnnnnnnn nnnnnnnnnn      8280
nnnnnnnnnn nnnnnnnnnn nnnnnnnnnn nnnnnnnnnn nnnnnnnnnn nnnnnnnnnn      8340
nnnnnnnnnn nnnnnnnnnn nnnnnnnnnn nnnnnnnnnn nnnnnnnnnn nnnnnnnnnn      8400
nnnnnnnnnn nnnnnnnnnn nnnnnnnnnn nnnnnnnnnn nnnnnnnnnn nnnnnnnnnn      8460
nnnnnnnnnn nnnnnnnnnn nnnnnnnnnn nnnnnnnnnn nnnnnnnnnn nnnnnnnnnn      8520
nnnnnnnnnn nnnnnnnnnn nnnnnnnnnn nnnnnnnnnn nnnnnnnnnn nnnnnnnnnn      8580
nnnnnnnnnn nnnnnnnnnn nnnnnnnnnn nnnnnnnnnn nnnnnnnnnn nnnnnnnnnn      8640
nnnnnnnnnn nnnnnnnnnn nnnnnnnnnn nnnnnnnnnn nnnnnnnnnn nnnnnnnnnn      8700
nnnnnnnnnn nnnnnnnnnn nnnnnnnnnn nnnnnnnnnn nnnnnnnnnn nnnnnnnnnn      8760
nnnnnnnnnn nnnnnnnnnn nnnnnnnnnn nnnnnnnnnn nnnnnnnnnn nnnnnnnnnn      8820
nnnnnnnnnn nnnnnnnnnn nnnnnnnnnn nnnnnnnnnn nnnnnnnnnn nnnnnnnnnn      8880
nnnnnnnnnn nnnnnnnnnn nnnnnnnnnn nnnnnnnnnn nnnnnnnnnn nnnnnnnnnn      8940
nnnnnnnnnn nnnnnnnnnn nnnnnnnnnn nnnnnnnnnn nnnnnnnnnn nnnnnnnnnn      9000
nnnnnnnnnn nnnnnnnnnn nnnnnnnnnn nnnnnnnnnn nnnnnnnnnn nnnnnnnnnn      9060
nnnnnnnnnn nnnnnnnnnn nnnnnnnnnn nnnnnnnnnn nnnnnnnnnn nnnnnnnnnn      9120
nnnnnnnnnn nnnnnnnnnn nnnnnnnnnn nnnnnnnnnn nnnnnnnnnn nnnnnnnnnn      9180
nnnnnnnnnn nnnnnnnnnn nnnnnnnnnn nnnnnnnnnn nnnnnnnnnn nnnnnnnnnn      9240
nnnnnnnnnn nnnnnnnnnn nnnnnnnnnn nnnnnnnnnn nnnnnnnnnn nnnnnnnnnn      9300
nnnnnnnnnn nnnnnnnnnn nnnnnnnnnn nnnnnnnnnn nnnnnnnnnn nnnnnnnnnn      9360
nnnnnnnnnn nnnnnnnnnn nnnnnnnnnn nnnnnnnnnn nnnnnnnnnn nnnnnnnnnn      9420
nnnnnnnnnn nnnnnnnnnn nnnnnnnnnn nnnnnnnnnn nnnnnnnnnn nnnnnnnnnn      9480
nnnnnnnnnn nnnnnnnnnn nnnnnnnnnn nnnnnnnnnn nnnnnnnnnn nnnnnnnnnn      9540
nnnnnnnnnn nnnnnnnnnn nnnnnnnnnn nnnnnnnnnn nnnnnnnnnn nnnnnnnnnn      9600
nnnnnnnnnn nnnnnnnnnn nnnnnnnnnn nnnnnnnnnn nnnnnnnnnn nnnnnnnnnn      9660
nnnnnnnnnn nnnnnnnnnn nnnnnnnnnn nnnnnnnnnn nnnnnnnnnn nnnnnnnnnn      9720
nnnnnnnnnn nnnnnnnnnn nnnnnnnnnn nnnnnnnnnn nnnnnnnnnn nnnnnnnnnn      9780
nnnnnnnnnn nnnnnnnnnn nnnnnnnnnn nnnnnnnnnn nnnnnnnnnn nnnnnnnnnn      9840
nnnnnnnnnn nnnnnnnnnn nnnnnnnnnn nnnnnnnnnn nnnnnnnnnn nnnnnnnnnn      9900
nnnnnnnnnn nnnnnnnnnn nnnnnnnnnn nnnnnnnnnn nnnnnnnnnn nnnnnnnnnn      9960
nnnnnnnnnn nnnnnnnnnn nnnnnnnnnn nnnnnnnnnn nnnnnnnnnn nnnnnnnnnn     10020
```

```
nnnnnnnnnn nnnnnnnnnn nnnnnnnnnn nnnnnnnnnn nnnnnnnnnn nnnnnnnnnn    10080
nnnnnnnnnn nnnnnnnnnn nnnnnnnnnn nnnnnnnnnn nnnnnnnnnn nnnnnnnnnn    10140
acacaatgca tgctcctgat gtccagagga cgtggtagaa aagacaggtt tggaggtggg    10200
agtgtggctg tctctattct ctgttgggaa aacctgggct gacaatattc agtggccatt    10260
tgtgggagtg aatcagccgg taagagctgt tctcagcctc tctaagggc agttcaggct     10320 cccagattga tccagactgt gtgtgacttt tgtccatttg acttgacttt ggaatagcac    10380
aagggcatca cgtacttcac gaggctttcc caatgtggct cagaggcagg agctctgatg    10440
ctctaggctg ctgtgaggtg gtggtggtgg tggagaaact ggcttcaccc acctactctt    10500
ctgtgaacag tagtgacttt tcccgctgtt tctcagcctc tgggatcaga gtcttcactg    10560 tctggctgg aaactttaag atagaatgga tagagcttcc acagtggttg gcatctagtg     10620
gtggatgaag acagcctgca gctgcccgac ttggggagct ctggagctcc tggaatcaaa    10680
gcctgtcttc caaccagaag ccccaaggca atgttctaag aatttgagaa gagaagttgg    10740
gagggaagtg gggtcctgag ttagagaccc atgaaggctg agtctaacca gataaccctg    10800
tccacagtgc aaagtcaaga cagccaaagg aacagaagat gtatttgtga aaactatttc    10860
ttttttaaga catggaacca actcaaattg gcctctatta gaaagacaat agattggctt    10920
aggtagggat gcatgctagg catacatcag gcaaggtttg atccaggaac tcacacagtg    10980
ccatcagctg tcctgtcttc tctgctctgc tcttctctcc tctgtgttaa tgccaccttc    11040
tcctcttcat acggtggcac tgagcagctt catgcctacc ttcctccagg gtcaagttca    11100
ttatcatgga cttgcctcat gctcagcagt cccagaaaaa agcctaattg caacttgatg    11160
gctttgttgg ctttctgagc aatgtgtcca gttgccacag tgaagggaat ggaataatct    11220
aactcaccat tcccaagtcc tatgccatcc tgagagtggg gggtggagtc aattcacctt    11280
ggtgcttgga ctaagcatga ggtggtgagt gacaacgttc ctaattgaag ggtagggtaa    11340
atggttgttg ggtggacacc aacacttatt ctactacaga agctaaattg aaccctcagg    11400
cagggtacgt gaaagtggca agagatgtca agaccactgg gcaagttggc cagttgttcc    11460
ttaggaatga aaattctttt gaaggaatg gccagggtcc tctgctggcc ccacttggtc      11520
ttctggaggc tctgatcttg gttggttagt ggtctttaca ggccaaggtc aaggccattg    11580
cacaaaaaac cctgtgcatg cccttaactt gctttcagtt gaatatttgg gctgaactat    11640
gaggcagaga ggaatcccat tgggtggctc cttgctgcat tcgcagttga ccagcatggg    11700
gtttgttgga gaaataggaa ccatcccctg aaaacacaca ctatggtagc cactcaactg    11760
ttgaaaggca ctggagtcca atgggtgagg ccgcctctga gacaagcctc tgagttgagg    11820
ctgggagagg ctccctcctt ggagtgttgc ttttttttgtt tcacccctgc ctctggagat    11880
gggtagagga acatgagctg accttctggg aagttaggtt ggtgaggagt tgctgaggca    11940
ctgcagggcc atgcccagta gagaggaatg tataacattt taagaggctg agagcacccc    12000
ttgttgggcg catgcccatg gcagcttcct tctgccgatc atgggagaaa tcaagcactt    12060
tcacctaatg gctagatgat tgattttggg atgaaattct ccactcctct cctttaccac    12120
atcaccacta tccttcctgc aatacatcca cgagactcac tgagtggaaa agggatagga    12180
atgaatgttc acccagggcc agctacatgc taggcactgt actggaccat ttaaatttgc    12240
cacctcttat gttcctcaca ttaatcttac agagtaggta cagacatacc tatggatatt    12300
gcagattcag ttccagacca cagcaataaa gcaagtcaca tgaatttttt gctttcctta    12360
```

```
gtgcatgtaa aagttacatt tccactatat tatagtttat taagtgtgca atagcattat   12420
gtctttaaaa agcatgtaca taccttaatt taaaaatacc ttgttgctga aaaatgctaa   12480
caatcatctg agccttcagt gattgcagta gcctaggcta ctattttcta tgtgggtttt   12540
gcacattctg cccatgtctg cgtgggtttt ctctgagttc tccagcttcc tcccacattc   12600
caaagatgtg tatgttacat tcatgggaat gtctaaattg tcgtaatctt tttgctggtt   12660
gatggtcttg ccttgatgtt gatgctgcag gtggtggttg ctgaaggtgg gggaggctgt   12720
ggcaatttct taaaataaaa taagacaaca gtggatttgc cacatcaatg gactcttcct   12780
ttcatgaaag atttctctgt agcagatgat gctgttctat agcattttac ccacagtaga   12840
atttcttttca aaactggagg tggtcctctc aaaccctatg ctactttatc gacgaagttt   12900
atgtagtatt ctaaatcttt tgttgtcatt tcaacagtgt tcatagcatt ttcacccaga   12960
gtagattcca tctcaagaaa ccacgatttt tgcttatctg taggaagcaa atcctcatct   13020
ggccaactta ttcatgagat tgaagcaatt cagtcatatt ttcaggctcc actcctaatt   13080
ctagttctct tgttatttcc accacatctg cagttacatc ttccactgaa gtcatgaacc   13140
cctcaaagtc atccataagg gttggaatca acttcttcca aactgttaat gatgttattt   13200
tgaccacctc ccataaatca tgaatgttcc tcatggcatc tggaatggtg aattctttttt  13260
agaagtttttc cagtttactt tgctgaggtc cataagagga ctcactgtct atgacaacta   13320
tagccttaca aattgtattt cttaaataat tggacttgaa agtcaaaata ctccttgatc   13380
cacaggctgc agaagggatg ttgtgtcagc aggcatgaac actactttaa ccttgtacat   13440
cttcatcaga gttctgggt tatcaagtgt cttgtaaata agcagtaata ttttcaaaga   13500
aatcttttat tctgagcagt aggtctcaac agtgggctta aaatatctag taaaccatgc   13560
tgtaaataga tgtgctggca cccaggcttc tttgttccat ttatagagca cagggaggct   13620
agatttagca taatttttca gggcccattc ttggaatgga aatgagcatt ggcttcaact   13680
taaagtcacc agctgcatta gctcctaaca agagagtcag cctgttcttt gaagctttga   13740
aggcaggcat tgacttcttc tctctagcta tgaaagccct agatggcatc ttcttcccat   13800
agaaggctgt ttcatctaca atgaaaatct tttgtttcat gtaatcacct tcatcaatca   13860
tcttaggtga gtctcctgga taccttgctg cagcttcccc atcagctctc cttcaccttg   13920
cacttttatg attatgttat ggagacaact tctttctttc aacctcttga accaaaccct   13980
ggctagcttc ctcacttccc cctcagccctt catggaatga aagagttagg ctcttcctct   14040
ggattaggct ttggtttaca ggaatgctgt ggctggtttg atctcctatt cagatcatta   14100
cattttcctg catgtcagca ataaggctgt ttttnnnnnn nnnnnnnnnn nnnnnnnnnn   14160
nnnnnnnnnn nnnnnnnnnn nnnnnnnnnn nnnnnnnnnn nnnnnnnnnn nnnnnnnnnn   14220
nnnnnnnnnn nnnnnnnnnn nnnnnnnnnn nnnnnnnnnn nnnnnnnnnn nnnnnnnnnn   14280
nnnnnnnnnn nnnnnnnnnn nnnnnnnnnn nnnnnnnnnn nnnnnnnnnn nnnnnnnnnn   14340
nnnnnnnnnn nnnnnnnnnn nnnnnnnnnn nnnnnnnnnn nnnnnnnnnn nnnnnnnnnn   14400
nnnnnnnnnn nnnnnnnnnn nnnnnnnnnn nnnnnnnnnn nnnnnnnnnn nnnnnnnnnn   14460
nnnnnnnnnn nnnnnnnnnn nnnnnnnnnn nnnnnnnnnn nnnnnnnnnn nnnnnnnnnn   14520
nnnnnnnnnn nnnnnnnnnn nnnnnnnnnn nnnnnnnnnn nnnnnnnnnn nnnnnnnnnn   14580
nnnnnnnnnn nnnnnnnnnn nnnnnnnnnn nnnnnnnnnn nnnnnnnnnn nnnnnnnnnn   14640
nnnnnnnnnn nnnnnnnnnn nnnnnnnnnn nnnnnnnnnn nnnnnnnnnn nnnnnnnnnn   14700
nnnnnnnnnn nnnnnnnnnn nnnnnnnnnn nnnnnnnnnn nnnnnnnnnn nnn          14753
```

```
<210> SEQ ID NO 4
<211> LENGTH: 358
<212> TYPE: PRT
<213> ORGANISM: Rat

<400> SEQUENCE: 4

Ile Tyr Ile Pro Leu Pro Asp Asp Ile Glu Pro Trp Lys Ile Ile
 1               5                  10                  15

Leu Gly Asn Thr Leu Leu Lys Leu Gly Gly Asp Leu Ala Ser Phe Gly
                20                  25                  30

Glu Leu Leu Gly Leu Asn His Phe Met Asp Thr Val Gln Leu Phe Met
             35                  40                  45

Arg Phe Gln Val Val Pro Pro Thr Ser Asp Glu Asn Val Thr Val Met
 50                  55                  60

Glu Thr Asp Phe Asn Ser Val Pro Val Arg Ile Tyr Ile Pro Lys Arg
 65                  70                  75                  80

Lys Ser Thr Thr Leu Arg Arg Gly Leu Phe Phe Ile His Gly Gly Gly
                 85                  90                  95

Trp Cys Leu Gly Ser Ala Ala Tyr Phe Met Tyr Asp Thr Leu Ser Arg
                100                 105                 110

Arg Thr Ala His Arg Leu Asp Ala Val Val Ser Thr Asp Tyr Gly
                115                 120                 125

Leu Ala Pro Lys Tyr His Phe Pro Lys Gln Phe Glu Asp Val Tyr His
    130                 135                 140

Ser Leu Arg Trp Phe Leu Gln Glu Asp Ile Leu Glu Lys Tyr Gly Val
145                 150                 155                 160

Asp Pro Arg Arg Val Gly Val Ser Gly Asp Ser Ala Gly Gly Asn Leu
                165                 170                 175

Thr Ala Ala Val Thr Gln Gln Ile Leu Gln Asp Pro Asp Val Lys Ile
                180                 185                 190

Lys Leu Lys Val Gln Ala Leu Ile Tyr Pro Ala Leu Gln Ala Leu Asp
            195                 200                 205

Met Asn Val Pro Ser Gln Gln Glu Asn Ser Gln Tyr Pro Leu Leu Thr
    210                 215                 220

Arg Ser Leu Leu Ile Arg Phe Trp Ser Glu Tyr Phe Thr Thr Asp Arg
225                 230                 235                 240

Asp Leu Glu Lys Ala Met Leu Leu Asn Gln His Val Pro Val Glu Phe
                245                 250                 255

Ser His Leu Leu Gln Phe Val Asn Trp Ser Ser Leu Leu Pro Gln Arg
            260                 265                 270

Tyr Lys Lys Gly Tyr Phe Tyr Lys Thr Pro Thr Pro Gly Ser Leu Glu
    275                 280                 285

Leu Ala Gln Lys Tyr Pro Gly Phe Thr Asp Val Lys Ala Cys Pro Leu
290                 295                 300

Leu Ala Asn Asp Ser Ile Leu His His Leu Pro Met Thr Tyr Ile Ile
305                 310                 315                 320

Thr Cys Gln Tyr Asp Val Leu Arg Asp Asp Gly Leu Met Tyr Val Lys
                325                 330                 335

Arg Leu Gln Asn Thr Gly Val His Val Thr His His Ile Glu Asp
                340                 345                 350

Gly Phe His Gly Ala Leu
            355
```

```
<210> SEQ ID NO 5
<211> LENGTH: 312
<212> TYPE: PRT
<213> ORGANISM: Mus musculus

<400> SEQUENCE: 5

Gln Leu Leu Met Ser Phe Gln Glu Val Pro Pro Thr Ser Asp Glu His
 1               5                  10                  15

Val Thr Val Met Glu Thr Ala Phe Asp Ser Val Pro Val Arg Ile Tyr
                20                  25                  30

Ile Pro Lys Arg Lys Ser Met Ala Leu Arg Arg Gly Leu Phe Tyr Ile
            35                  40                  45

His Gly Gly Gly Trp Cys Leu Gly Ser Ala Ala His Phe Ser Tyr Asp
     50                  55                  60

Thr Leu Ser Arg Trp Thr Ala His Lys Leu Asp Ala Val Val Val Ser
65                  70                  75                  80

Thr Asp Tyr Gly Leu Ala Pro Lys His His Phe Pro Arg Gln Phe Glu
                85                  90                  95

Asp Val Tyr Arg Ser Leu Arg Trp Phe Leu Gln Glu Asp Val Leu Glu
                100                 105                 110

Lys Tyr Gly Val Asp Pro Arg Arg Val Gly Val Ser Gly Asp Ser Ala
            115                 120                 125

Gly Gly Asn Leu Ala Ala Ala Val Thr Gln Gln Leu Ile Gln Asp Pro
    130                 135                 140

Asp Val Lys Ile Lys Leu Lys Val Gln Ala Leu Ile Tyr Pro Ala Leu
145                 150                 155                 160

Gln Ala Leu Asp Thr Asn Val Pro Ser Gln Gln Glu Gly Ser His Phe
                165                 170                 175

Pro Val Leu Thr Arg Ser Leu Met Val Arg Phe Trp Ser Glu Tyr Phe
                180                 185                 190

Thr Thr Asp Arg Gly Leu Glu Lys Ala Met Leu Leu Asn Gln His Val
            195                 200                 205

Pro Met Glu Ser Ser His Leu Leu Gln Phe Val Asn Trp Ser Ser Leu
    210                 215                 220

Leu Pro Glu Arg Tyr Lys Lys Ser Pro Val Tyr Lys Asn Pro Thr Pro
225                 230                 235                 240

Gly Ser Ser Glu Leu Ala Gln Lys Tyr Pro Gly Phe Ile Asp Val Lys
                245                 250                 255

Ala Cys Pro Leu Leu Ala Asn Asp Asn Ile Leu His His Leu Pro Lys
                260                 265                 270

Thr Tyr Ile Ile Thr Cys Gln Tyr Asp Val Leu Arg Asp Asp Gly Leu
            275                 280                 285

Met Tyr Val Lys Arg Leu Gln Asn Val Gly Val His Val Thr His His
    290                 295                 300

His Val Glu Asp Gly Phe His Gly
305                 310
```